United States Patent [19]

Kondo et al.

[11] Patent Number: 5,766,131
[45] Date of Patent: Jun. 16, 1998

[54] PULSE-WAVE MEASURING APPARATUS

[75] Inventors: Yutaka Kondo; Katsuyuki Honda, both of Suwa; Hiroshi Odagiri; Takeshi Ono, both of Chiba, all of Japan

[73] Assignees: Seiko Epson Corporation, Tokyo; Seiko Instruments, Inc., Chiba, both of Japan

[21] Appl. No.: 692,897

[22] Filed: Jul. 30, 1996

[30] Foreign Application Priority Data

Aug. 4, 1995 [JP] Japan .................. 7-199813
Oct. 20, 1995 [JP] Japan .................. 7-273240
Oct. 20, 1995 [JP] Japan .................. 7-273241

[51] Int. Cl.$^6$ ............................................. A61B 5/02
[52] U.S. Cl. .................. 600/502; 600/344; 600/503; 600/310
[58] Field of Search .............................. 128/633, 639, 128/664–667, 687–690; 600/310, 323, 344, 503, 502, 473–480

[56] References Cited

U.S. PATENT DOCUMENTS

| | | | |
|---|---|---|---|
| 4,280,506 | 7/1981 | Zurcher | 128/690 |
| 4,332,258 | 6/1982 | Arai et al. | 128/687 |
| 4,425,921 | 1/1984 | Fujisaki et al. | 128/690 |
| 4,807,639 | 2/1989 | Shimizu et al. | |
| 4,825,872 | 5/1989 | Tan et al. | |
| 4,971,062 | 11/1990 | Hasebe et al. | 128/664 |
| 5,080,098 | 1/1992 | Willett et al. | 128/633 |
| 5,125,403 | 6/1992 | Culp | 128/633 |
| 5,224,478 | 7/1993 | Sakai et al. | 128/666 |
| 5,452,717 | 9/1995 | Branigan et al. | 128/666 |
| 5,511,546 | 4/1996 | Hon | 128/666 |

FOREIGN PATENT DOCUMENTS

| | | |
|---|---|---|
| 2 583 282 | 12/1986 | France . |
| 19 09 882 | 9/1970 | Germany . |
| 2 052 051 | 1/1981 | United Kingdom . |

*Primary Examiner*—Lee S. Cohen
*Assistant Examiner*—David M. Ruddy
*Attorney, Agent, or Firm*—Michael T. Gabrik

[57] ABSTRACT

To achieve a pulse wave measuring apparatus whereby the sensor unit can be easily and consistently worn against the skin surface, a wristwatch type pulse wave measuring apparatus is comprised as follows. Specifically, light transmittance plate 34 is disposed on the outside surface side of LED 31 and phototransistor 32 in sensor unit 30. Outside surface 341 of light transmittance plate 34, which is pressed against the finger, projects above the reference surface, which is outside surface 361 of sensor frame 36 surrounding light transmittance plate 34. Two body ground terminals 38 contacting the finger when light transmittance plate 34 is pressed tight to the finger are disposed around light transmittance plate 34; the body ground terminals 38 also project above the reference surface. However, the position of outside surfaces 381 of body ground terminals 38 is lower than the outside surface 341 of light transmittance plate 34. A supporter-like sensor unit holding band is used to hold sensor unit 30 on the finger. A thick material such as that used in diving wet suits is used for the sensor unit holding band, and comprises a middle layer of foam rubber.

19 Claims, 32 Drawing Sheets

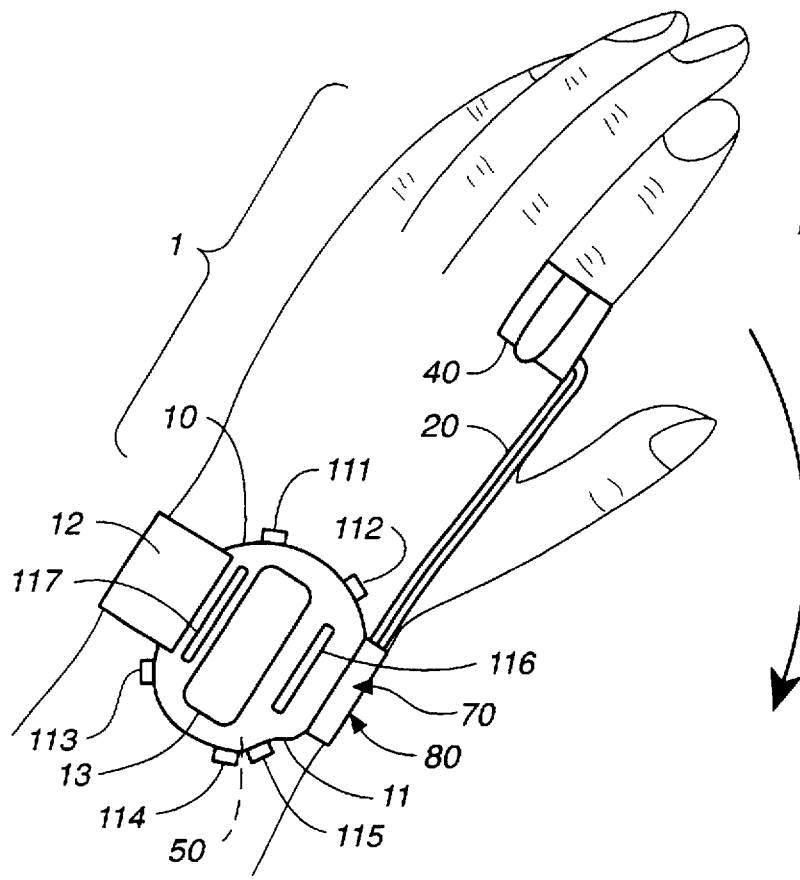
FIG._1A
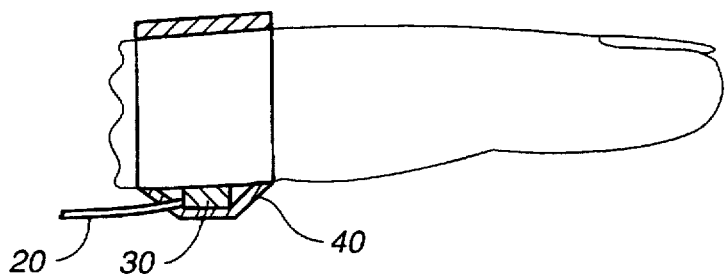
FIG._1B

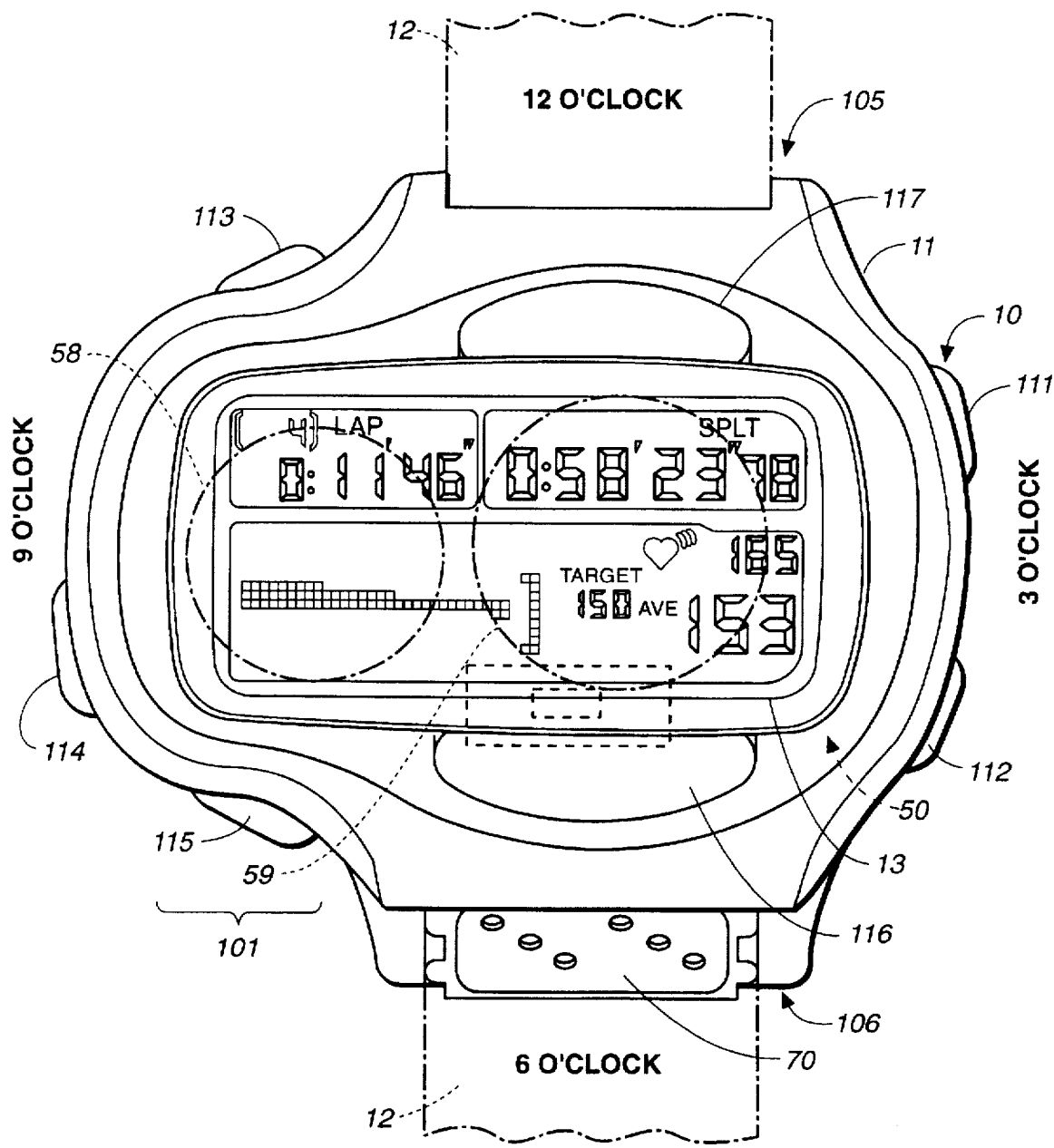
FIG._2

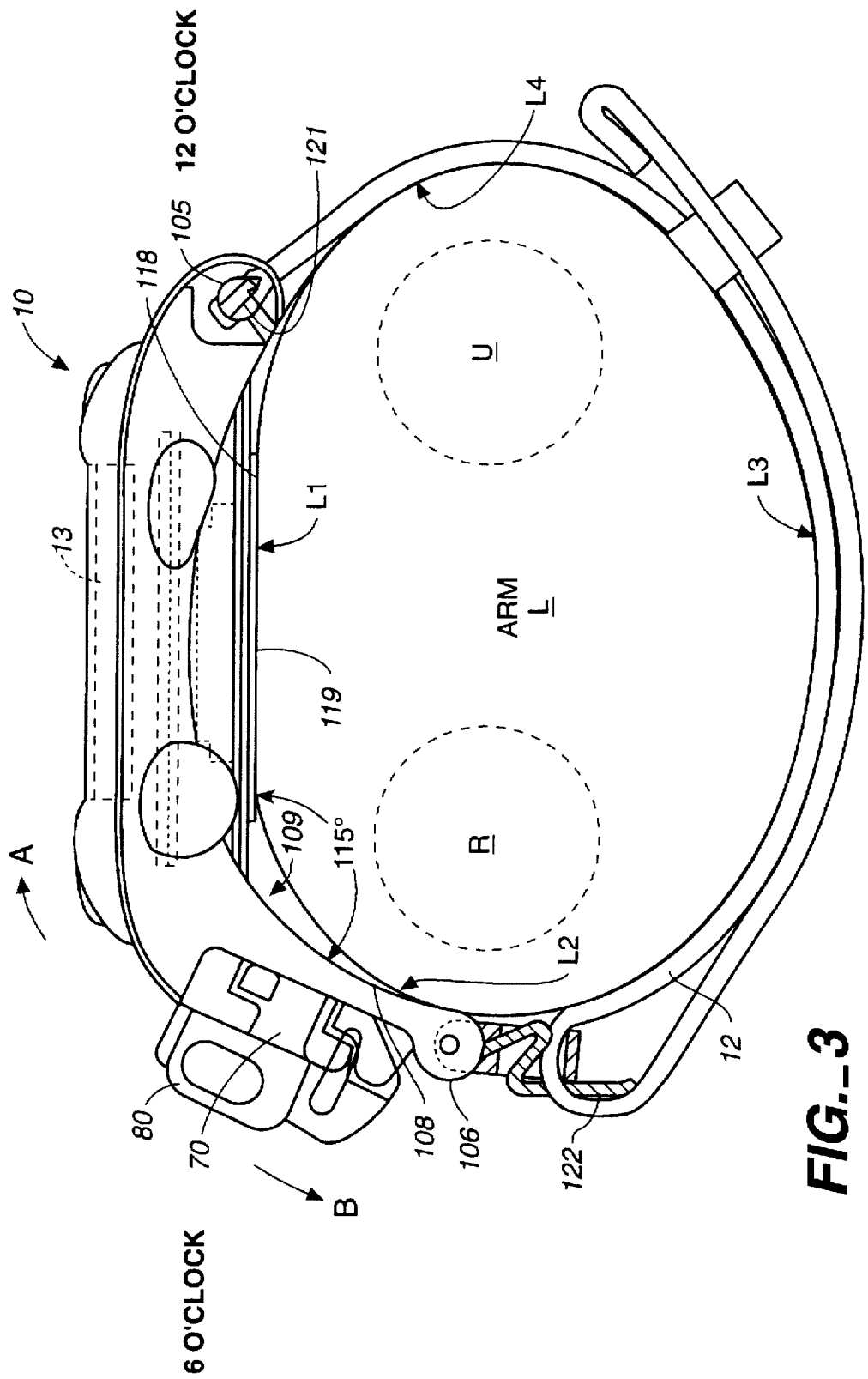
FIG._3

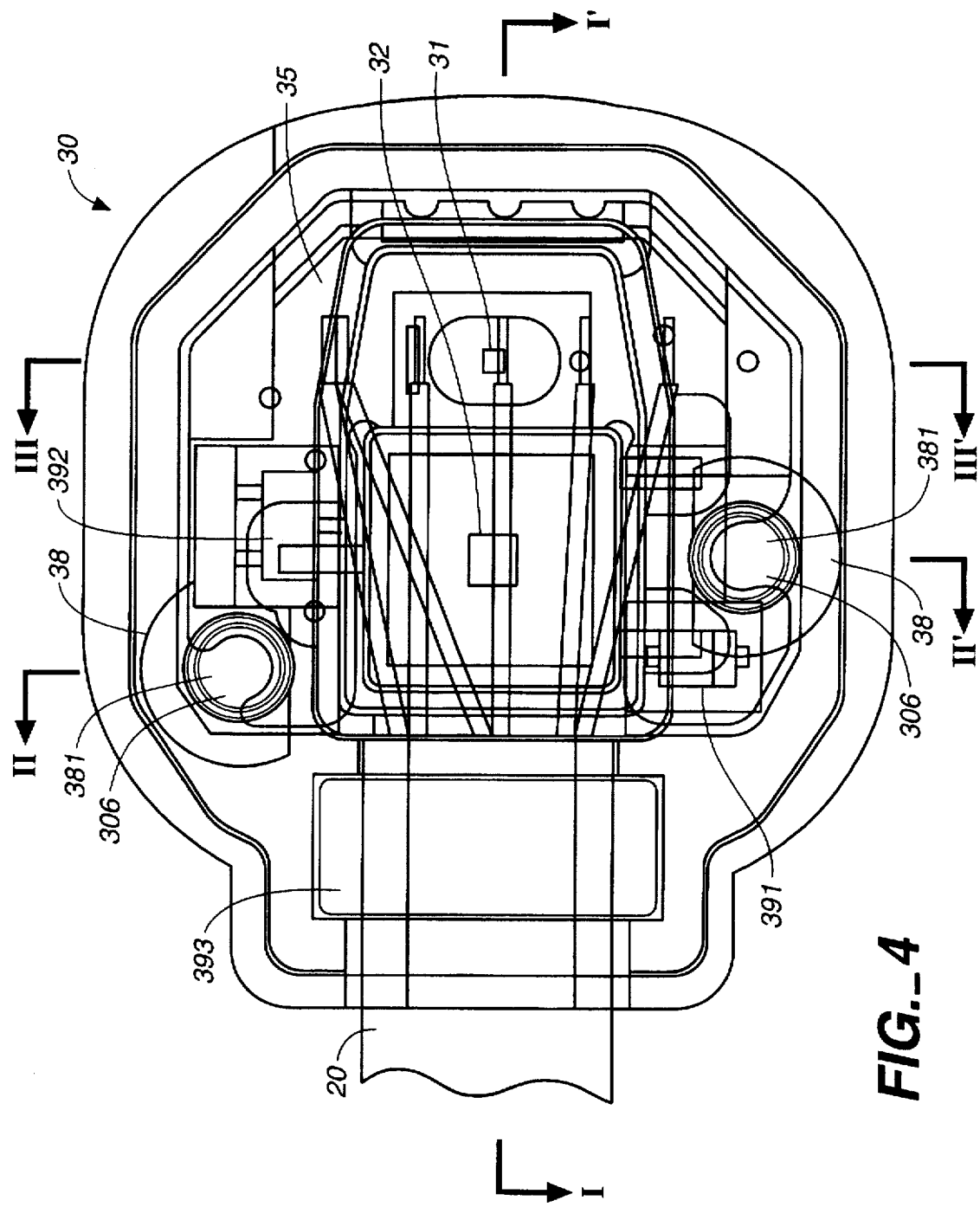
FIG._4

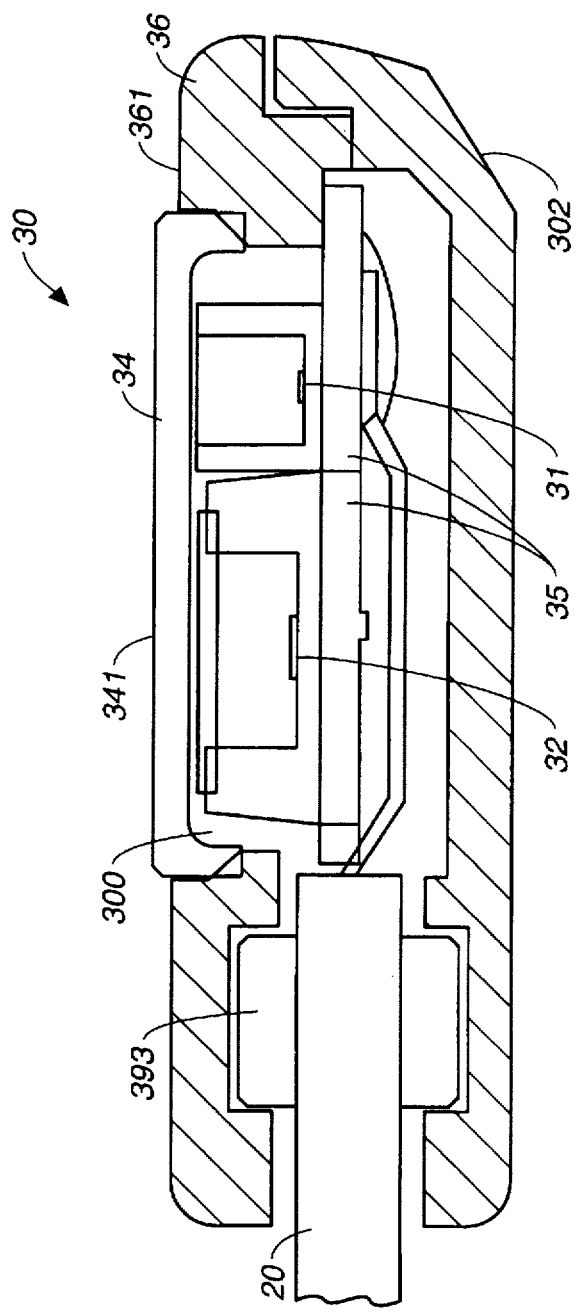
FIG._5

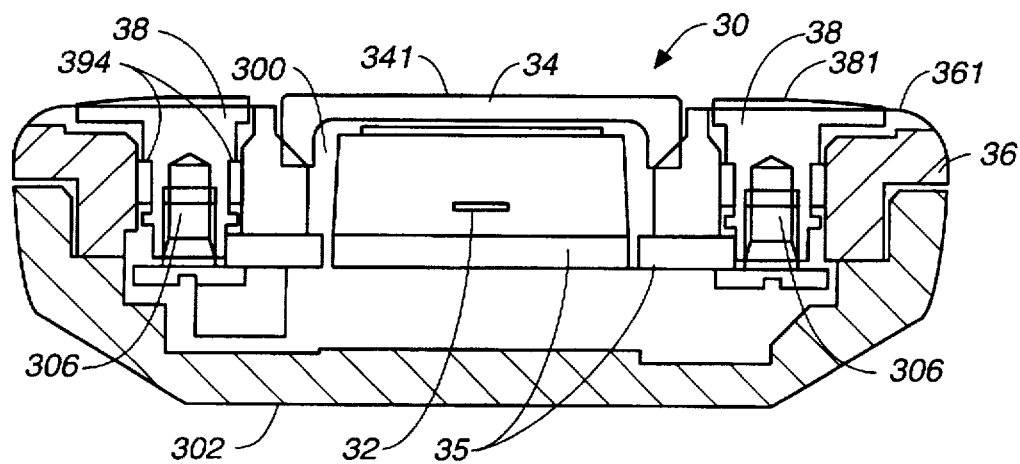
FIG._6
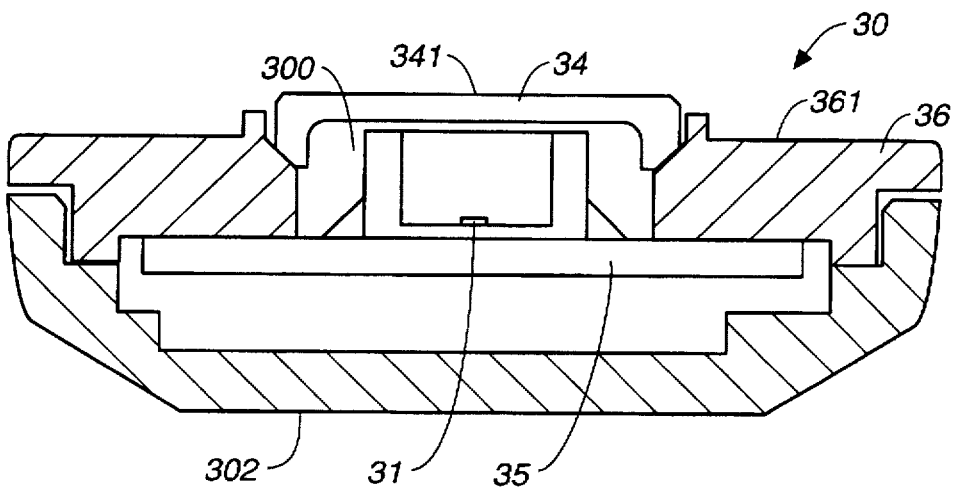
FIG._7

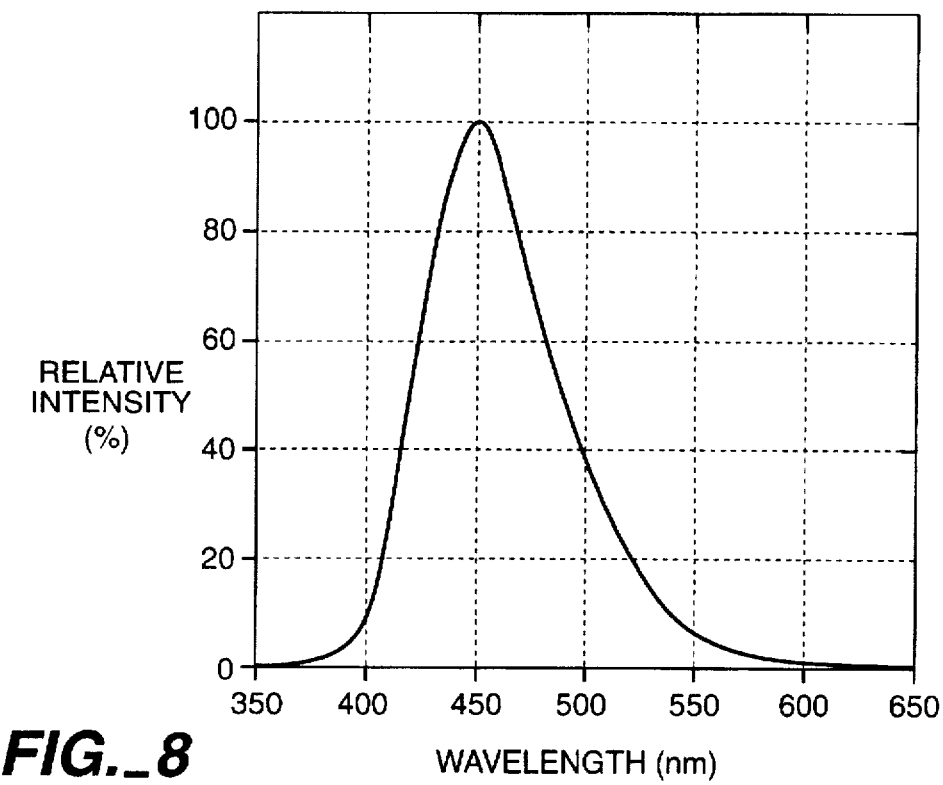
FIG._8
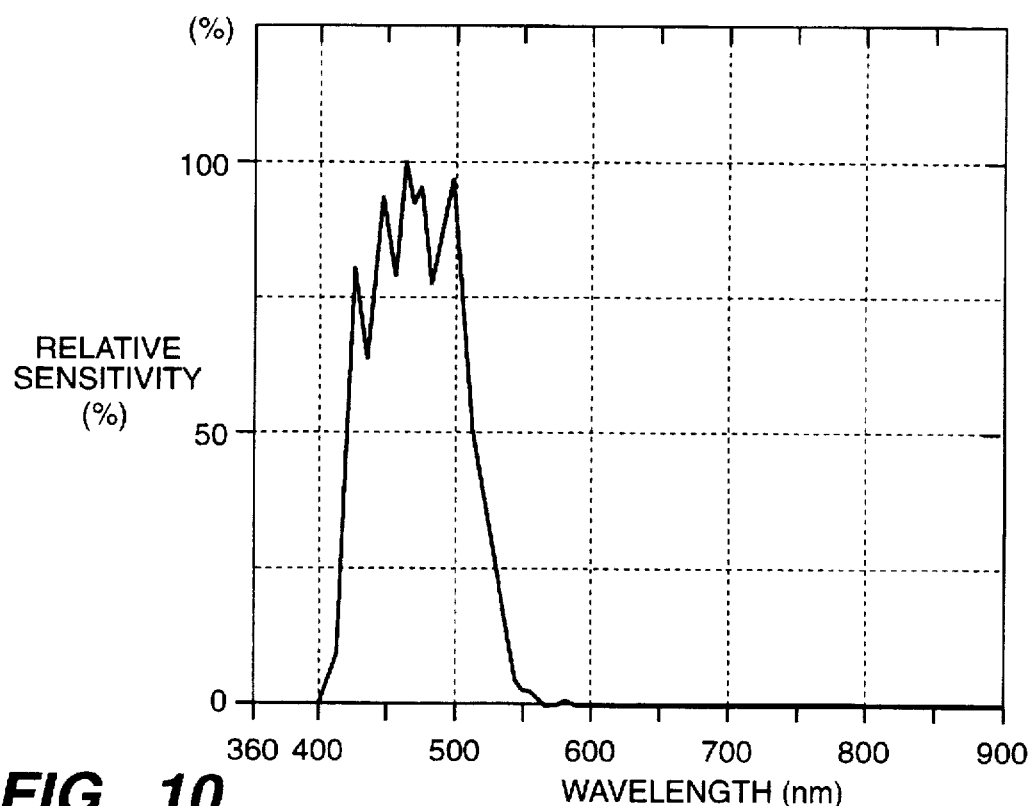
FIG._10

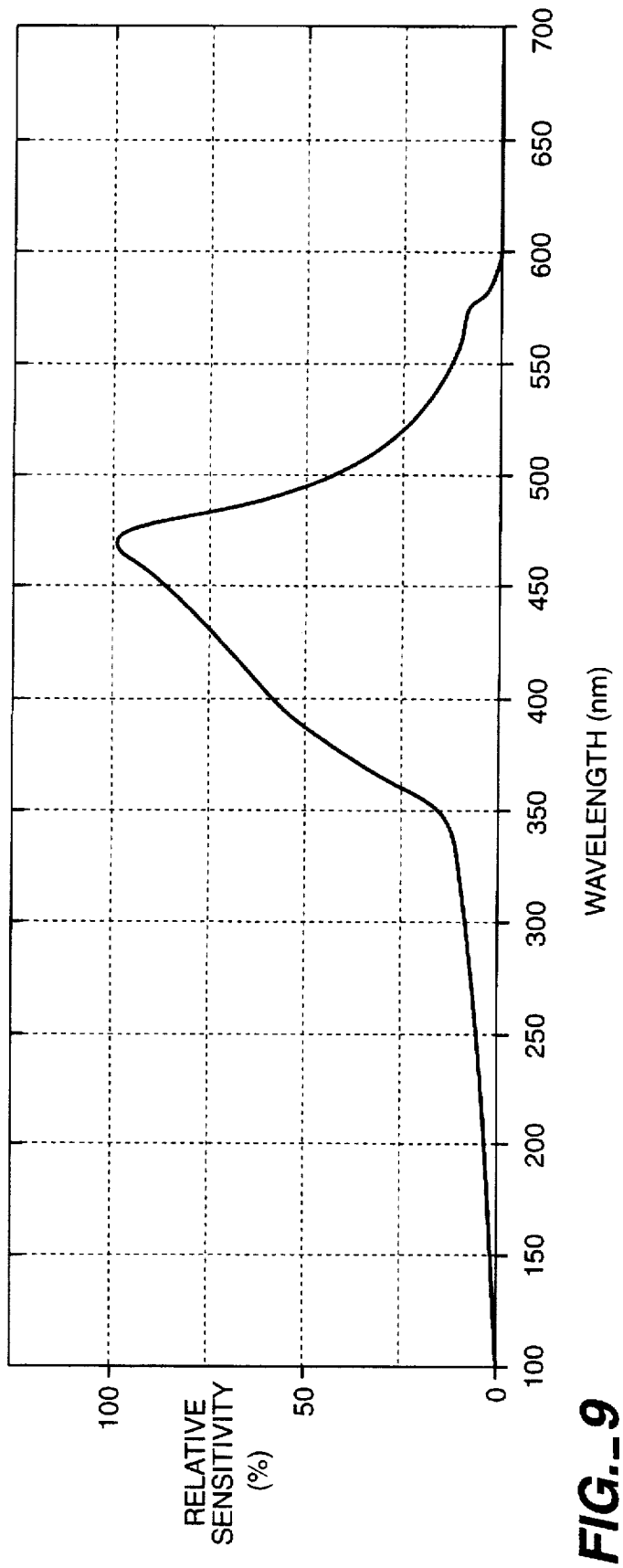
FIG._9
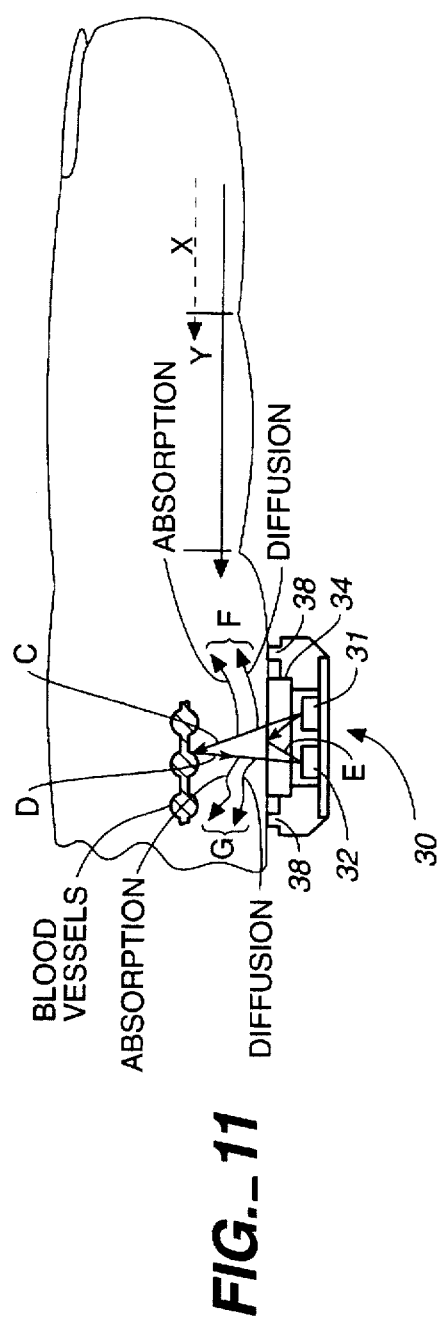
FIG._11

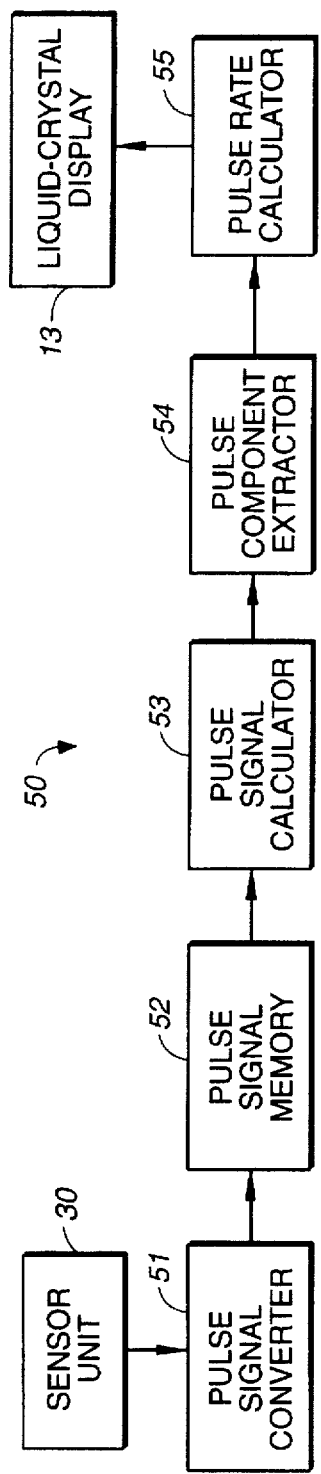
FIG._12
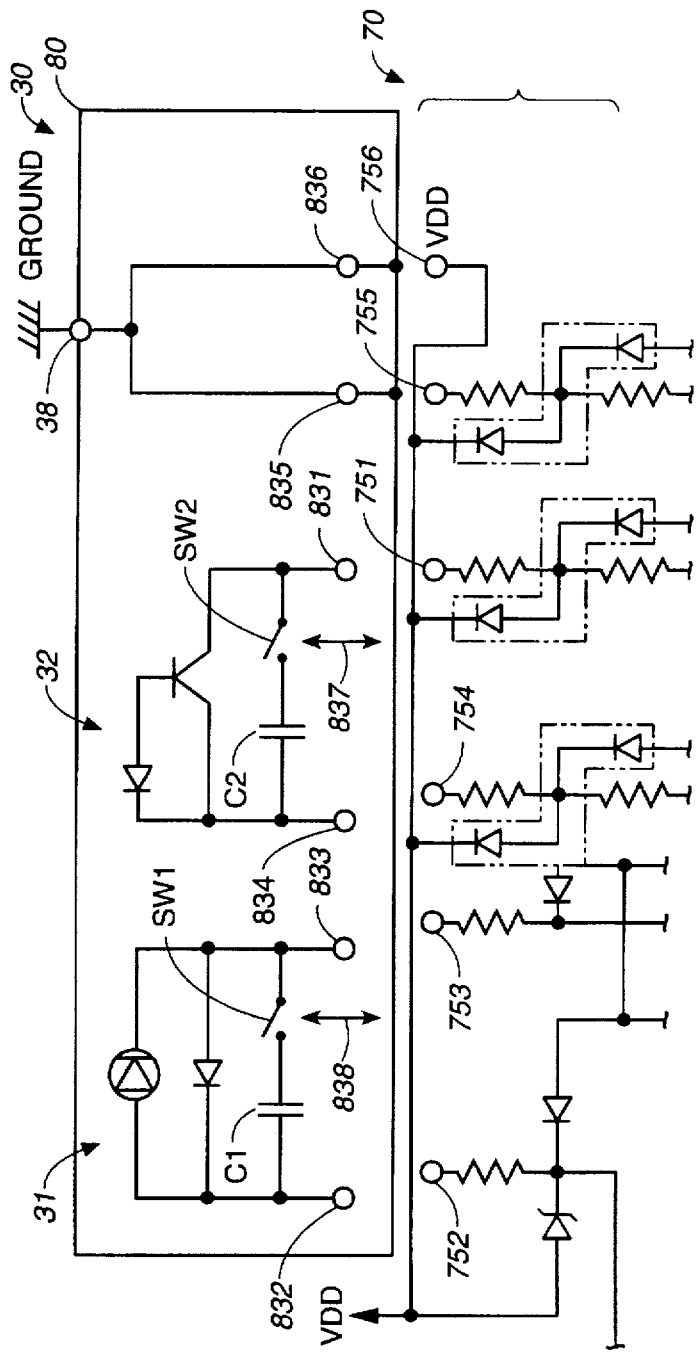
FIG._13

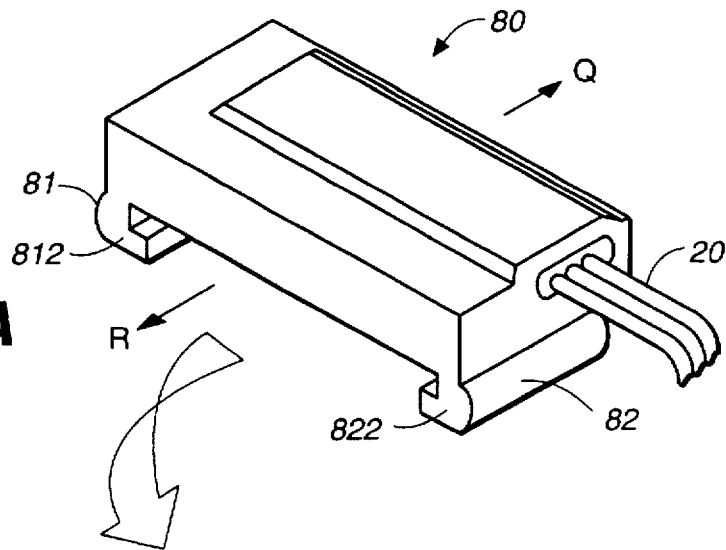
FIG._14A
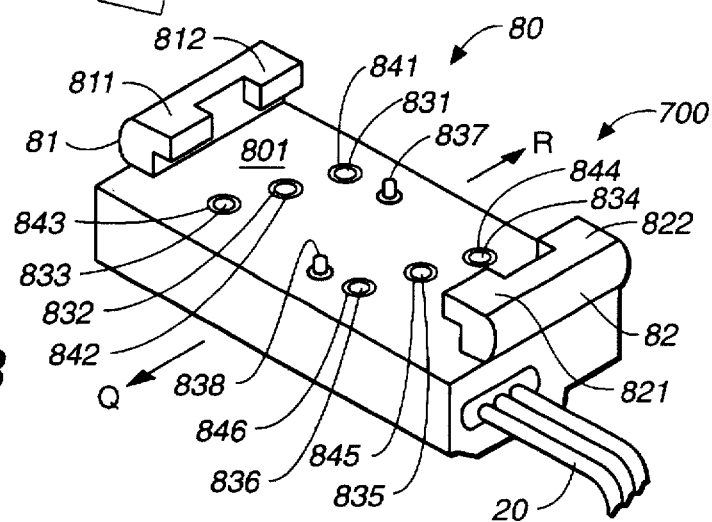
FIG._14B
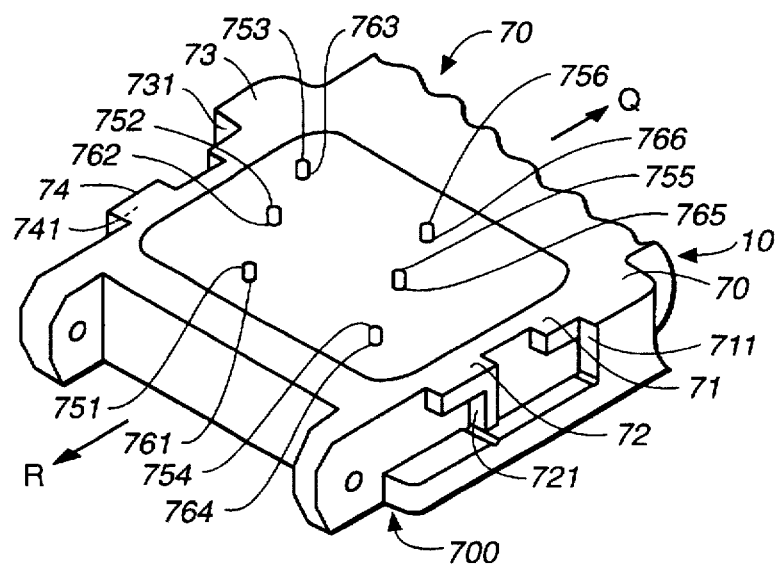
FIG._15

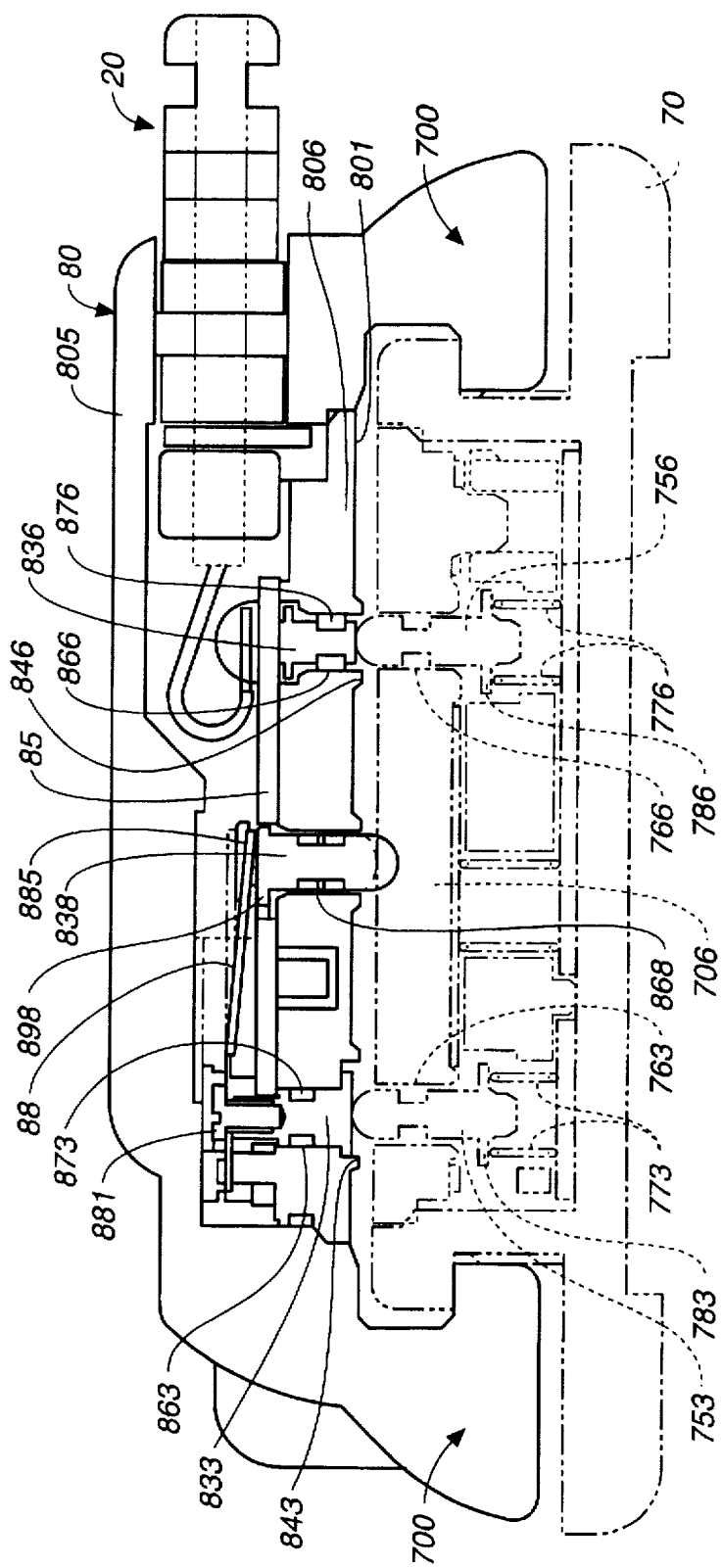
FIG._16

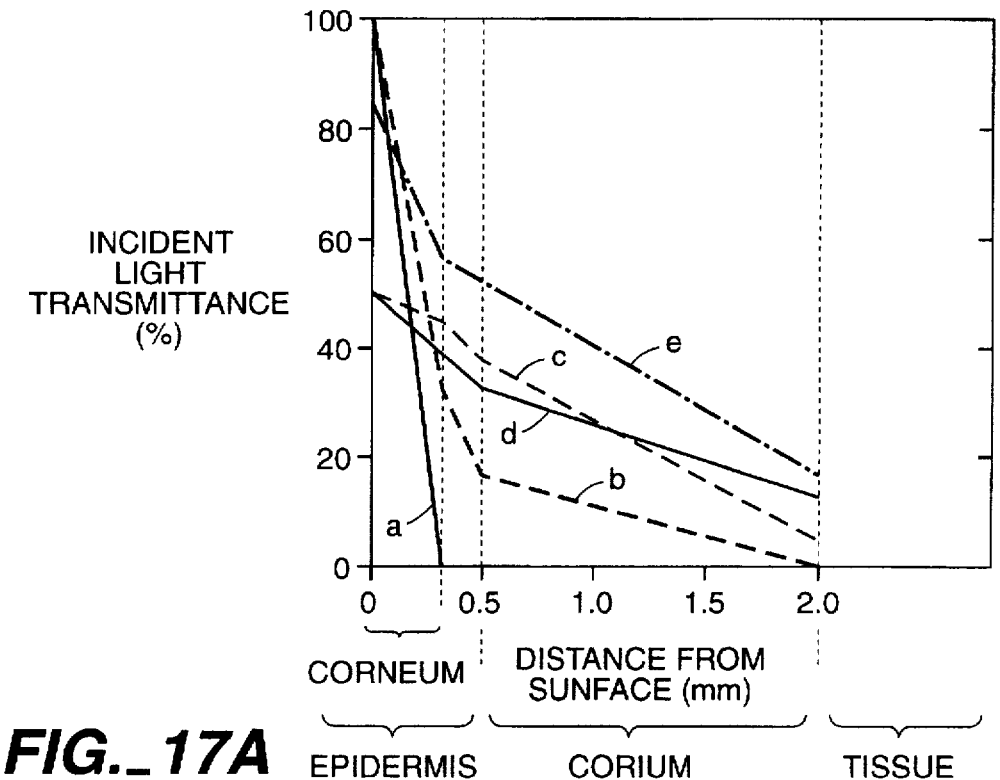
FIG._17A
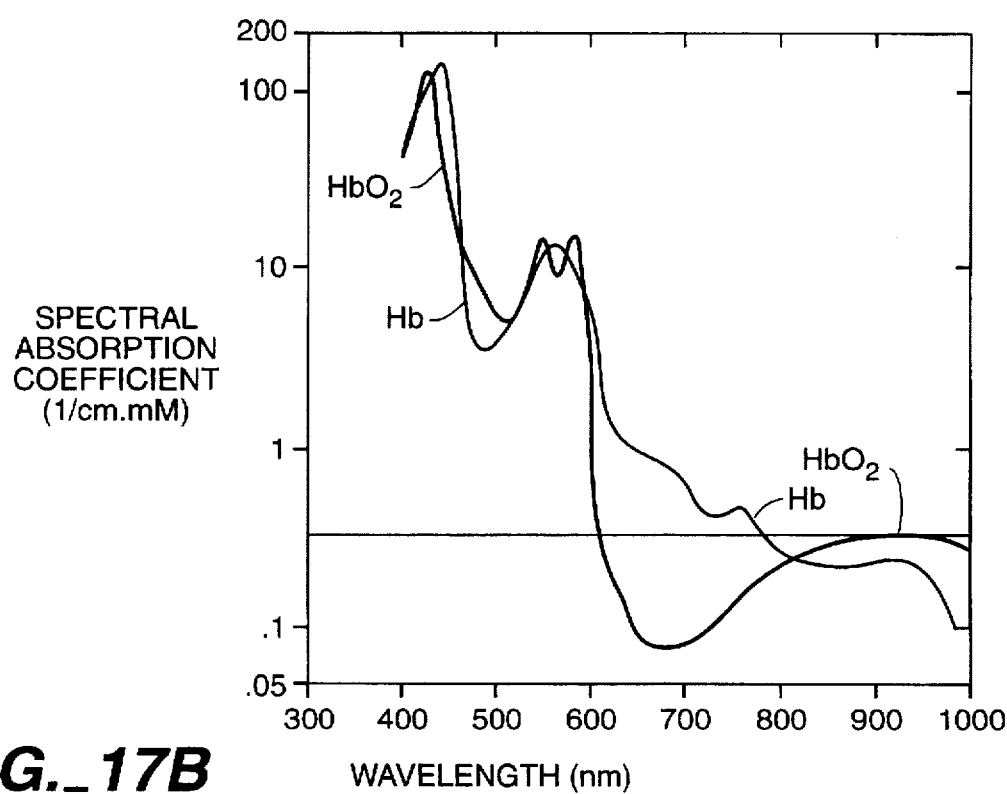
FIG._17B

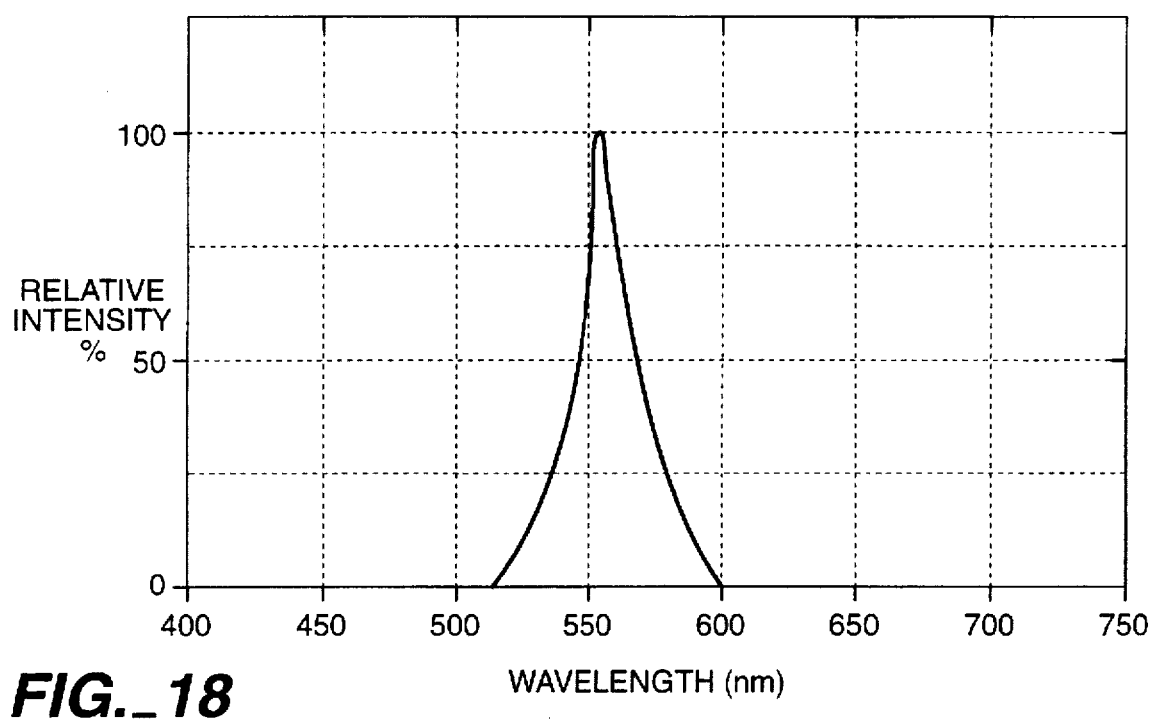
FIG._18
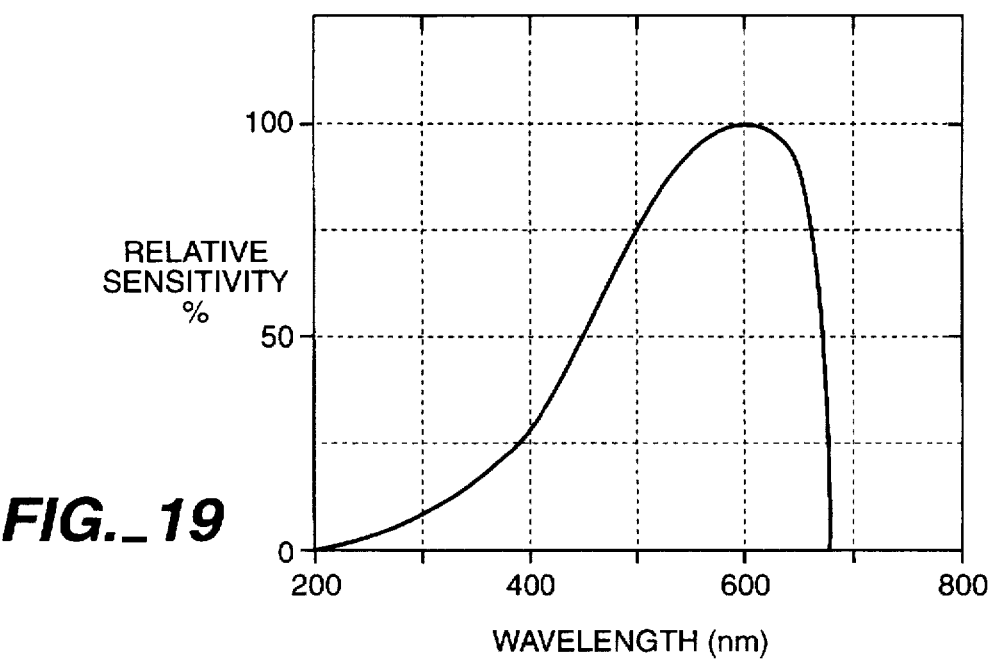
FIG._19

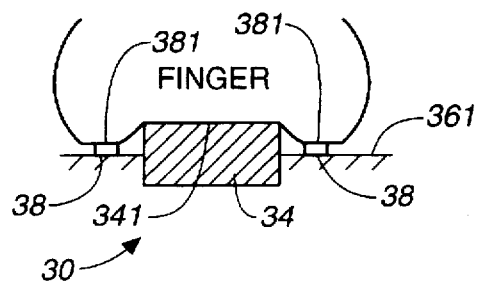
*FIG._20A-1*
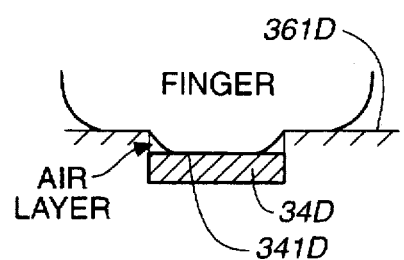
*FIG._20B-1*
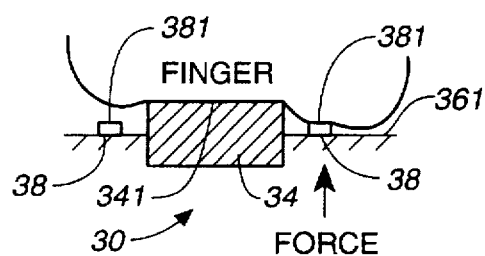
*FIG._20A-2*
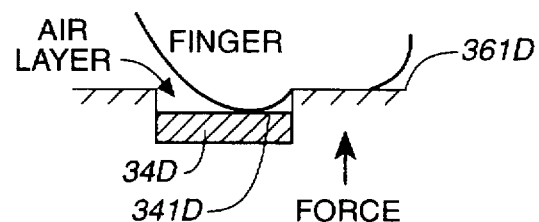
*FIG._20B-2*
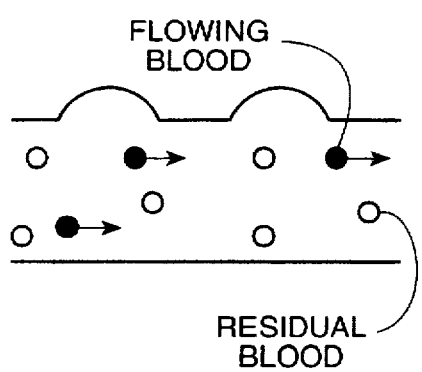
*FIG._21A*
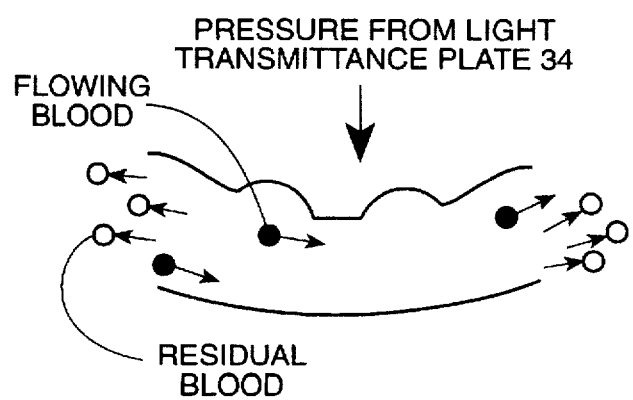
*FIG._21B*

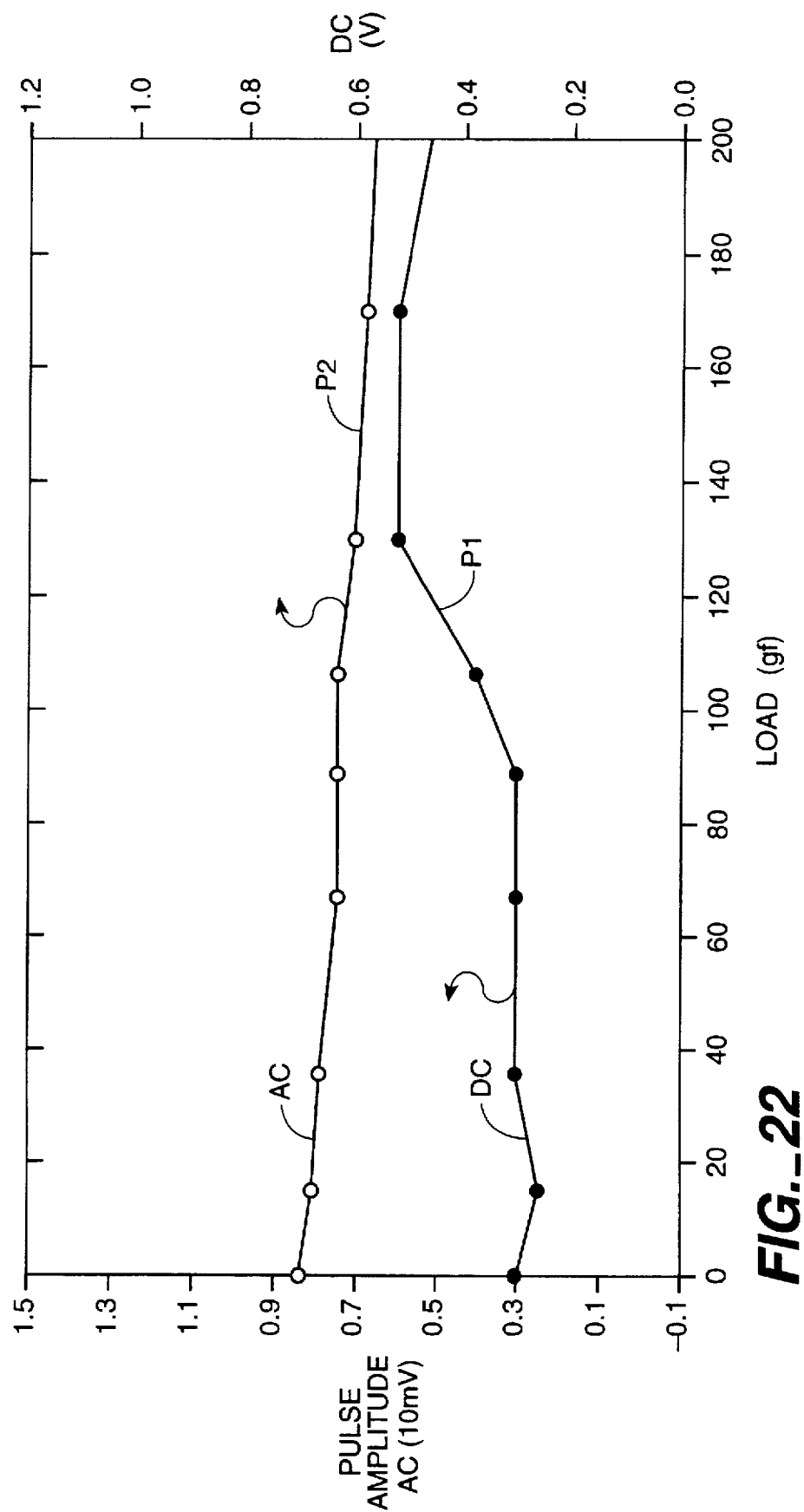
FIG._22

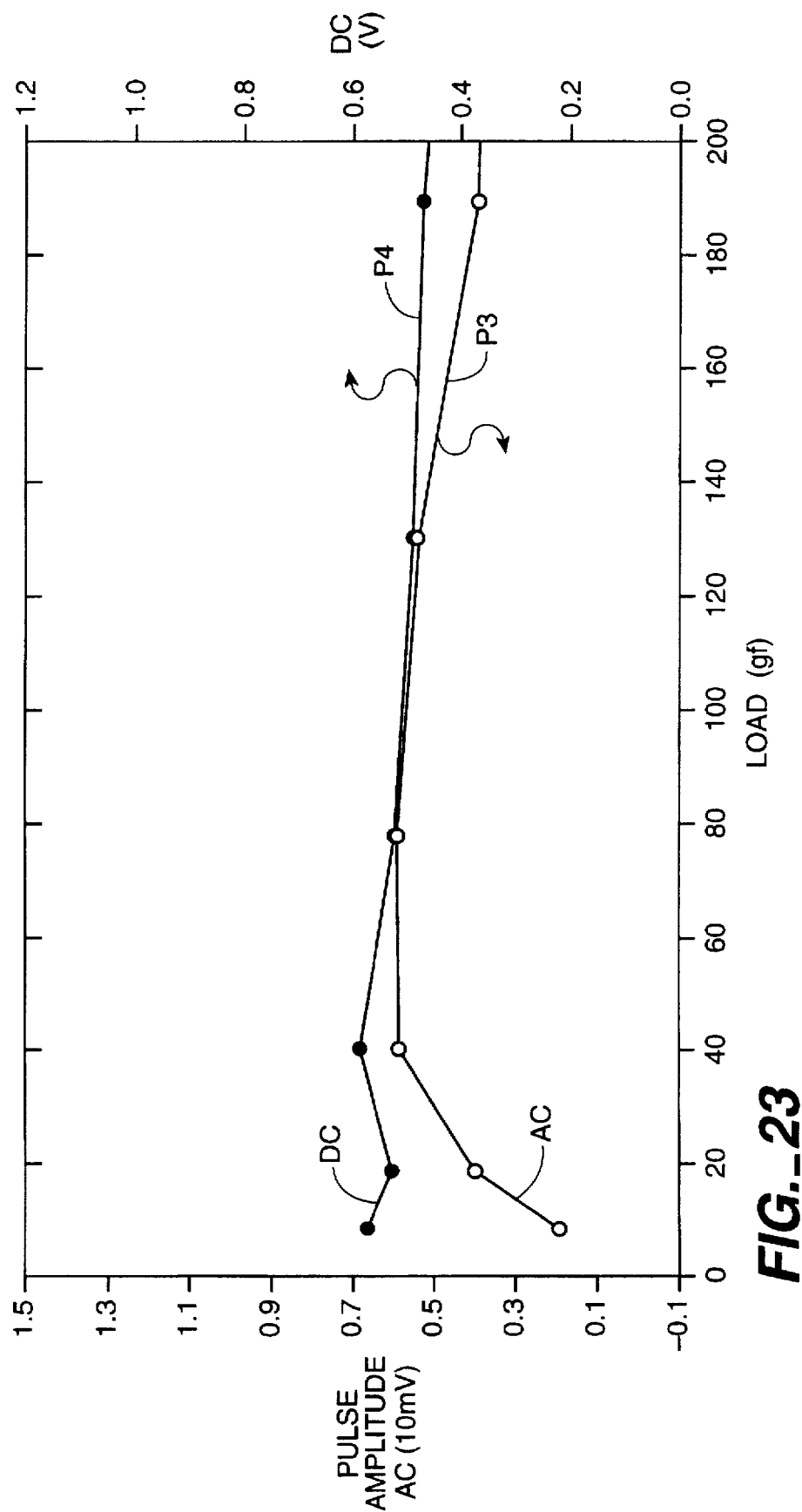
FIG._23

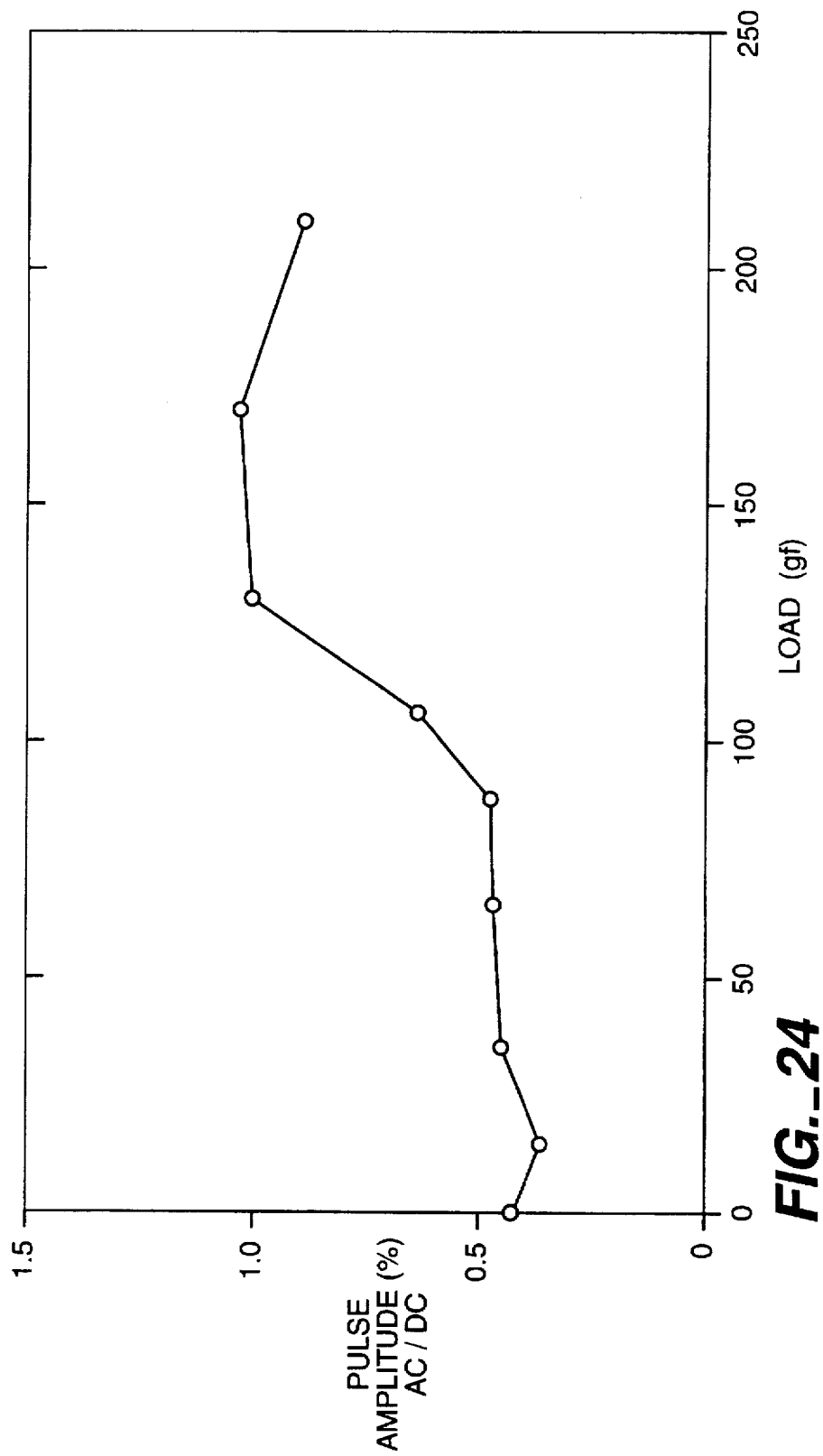
FIG._24

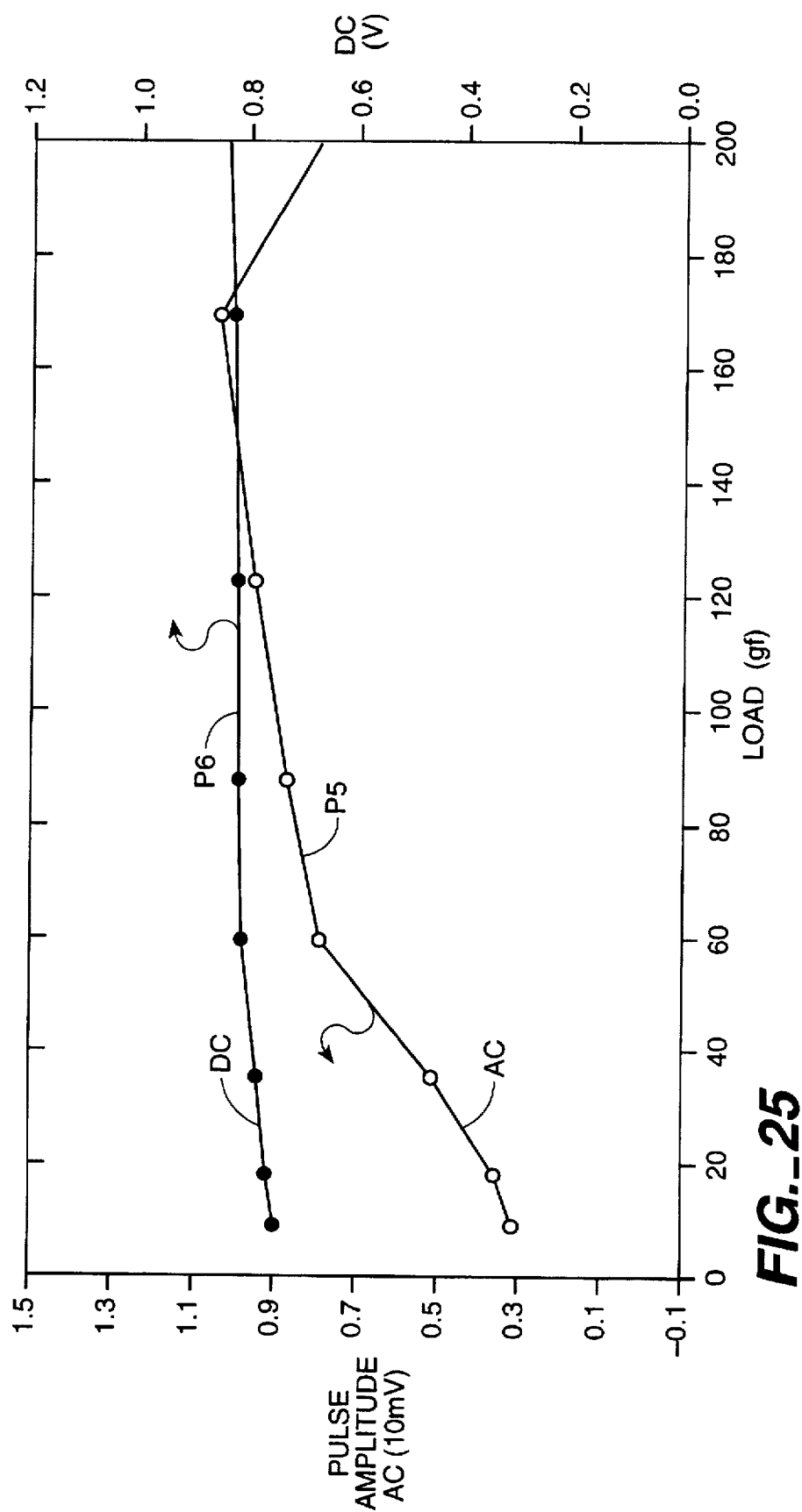
FIG._25

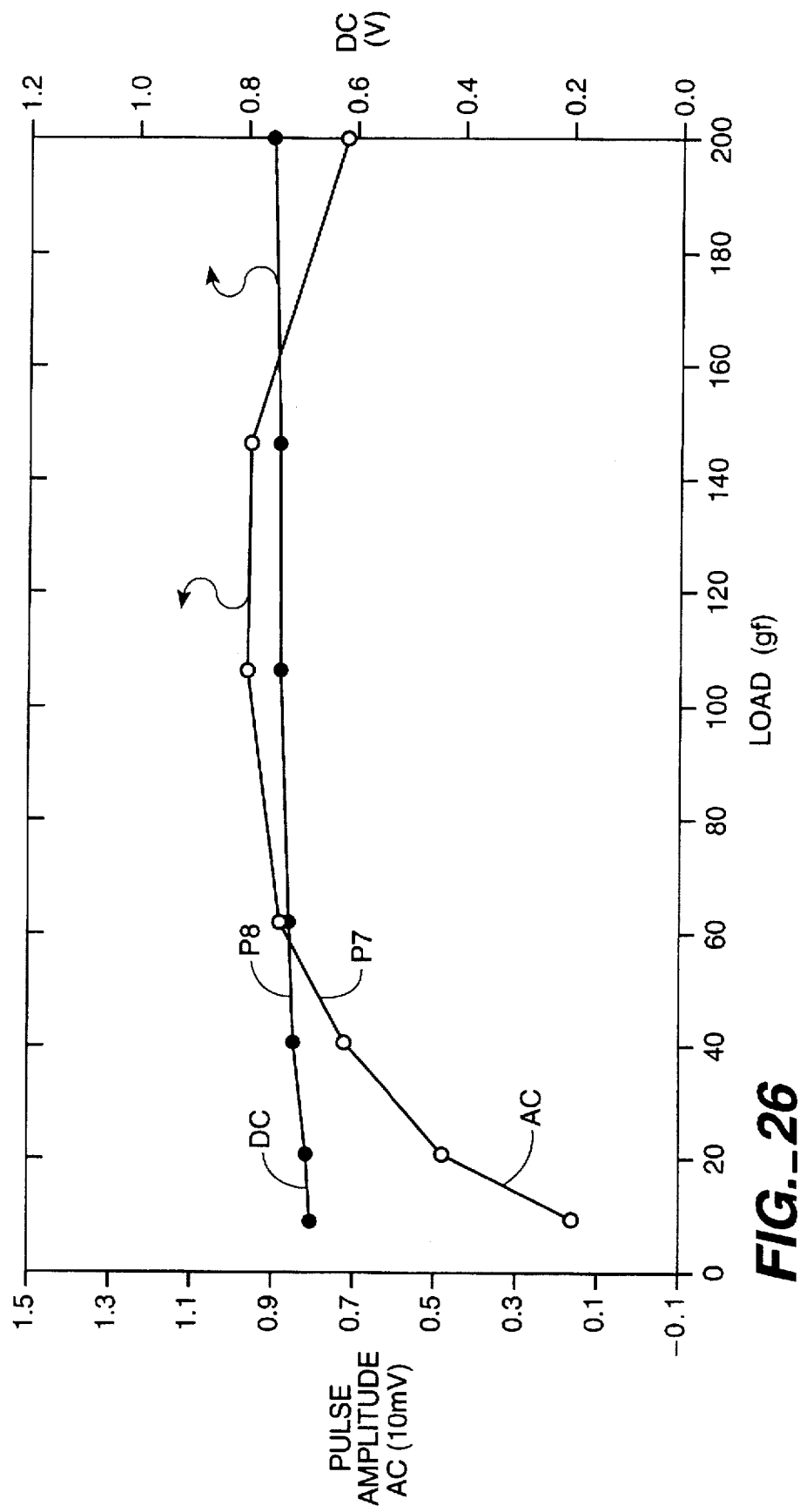
FIG._26

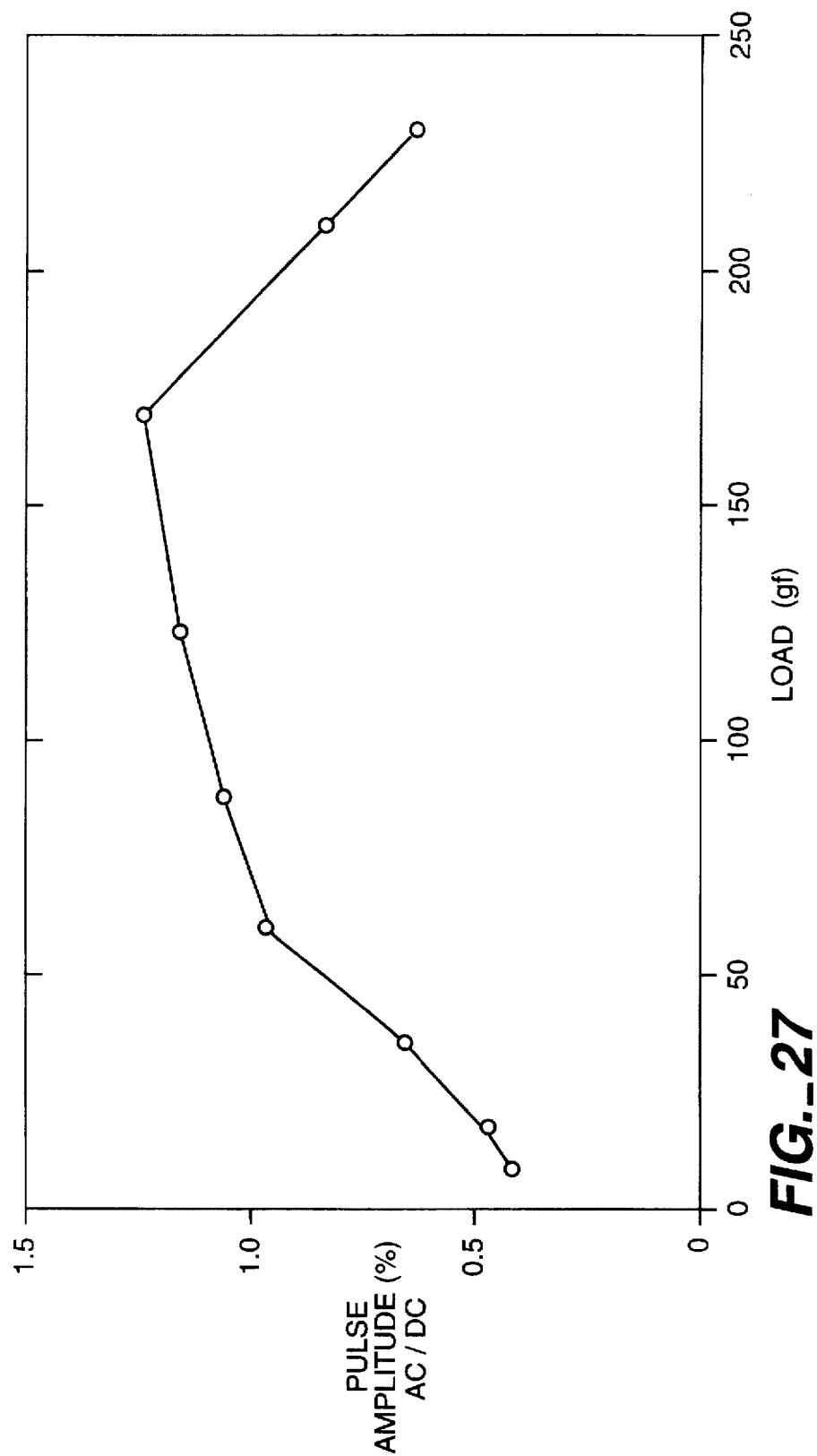
FIG._27

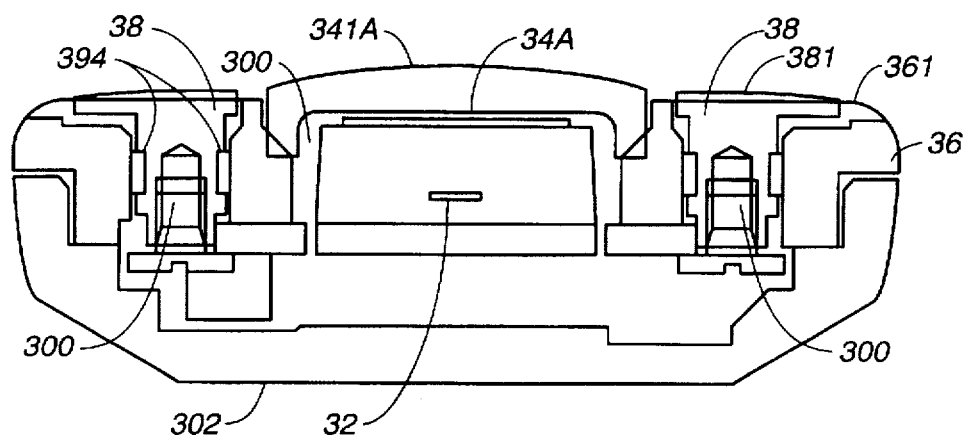
FIG._28
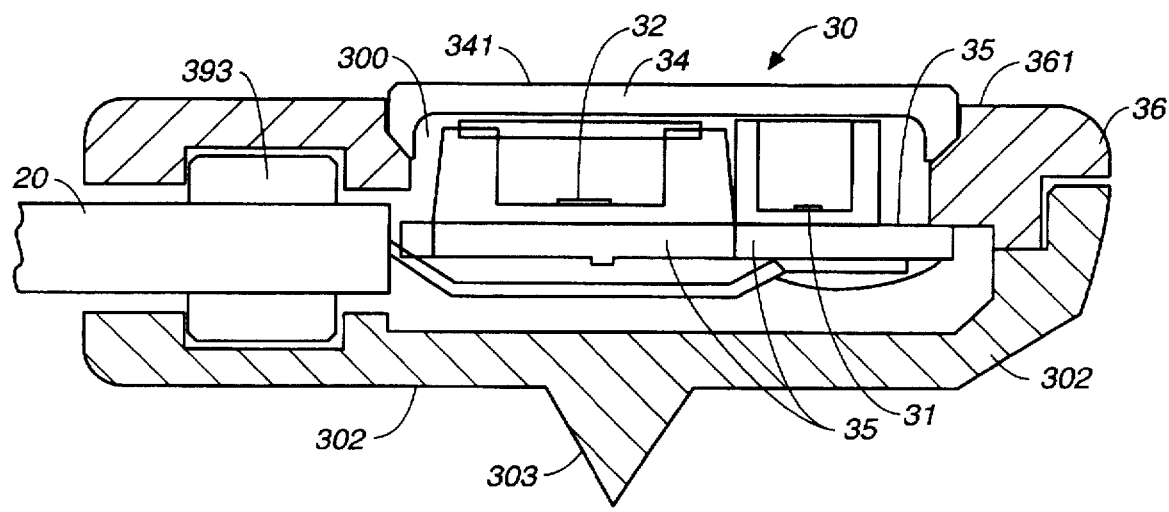
FIG._29

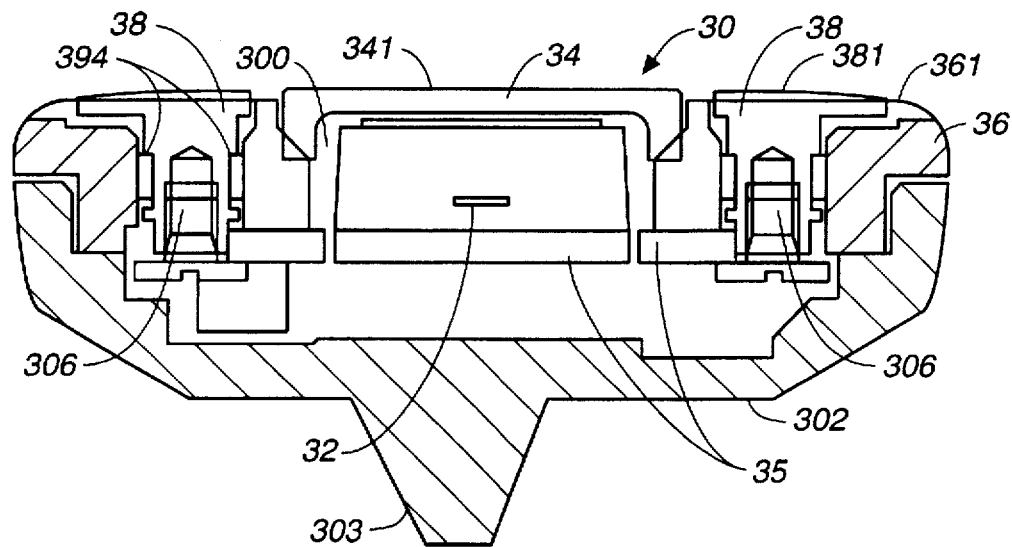
FIG._30
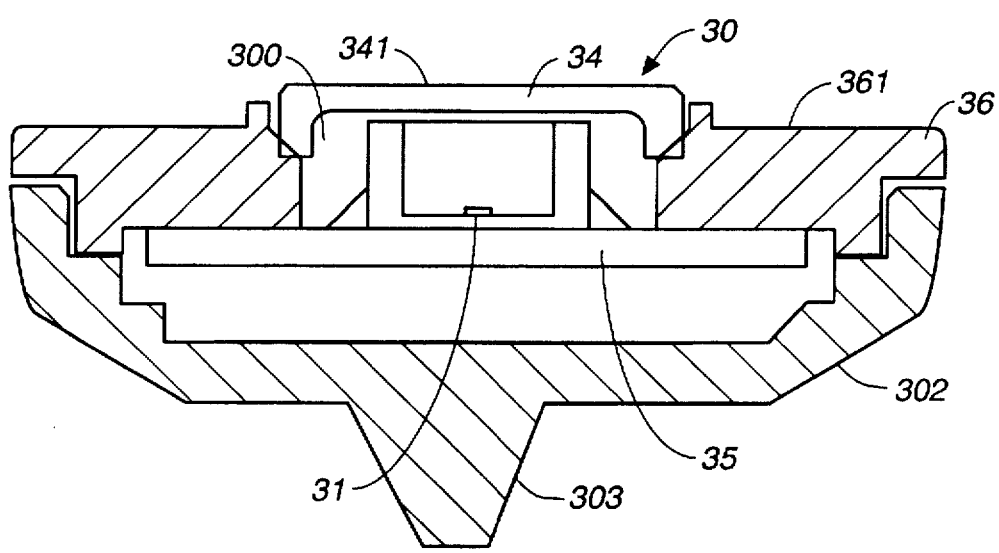
FIG._31

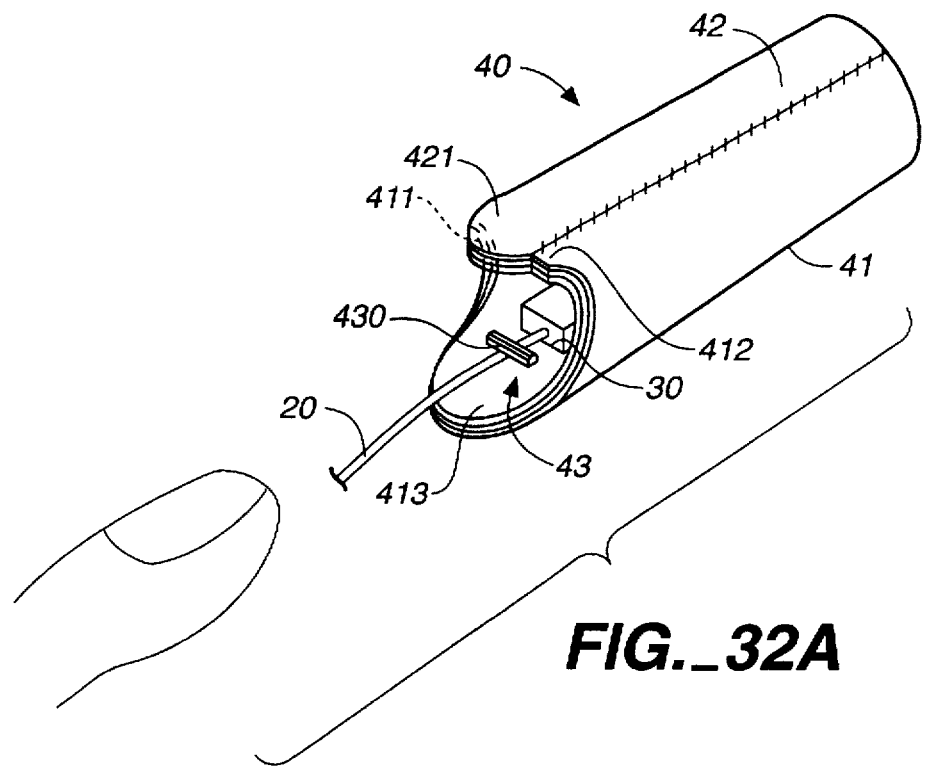
FIG._32A
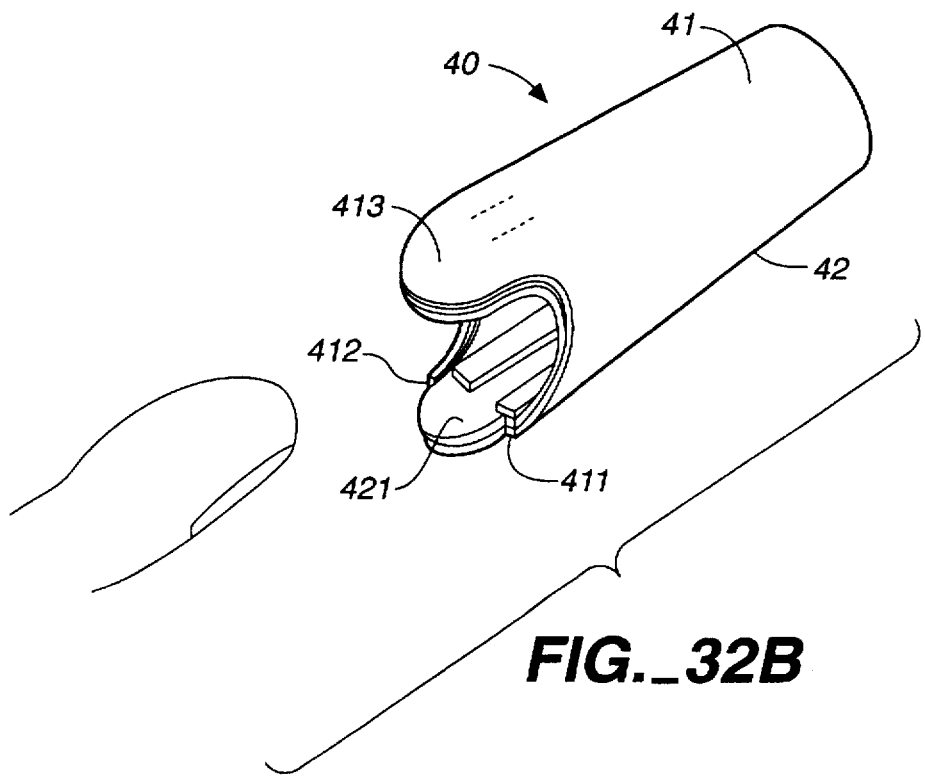
FIG._32B

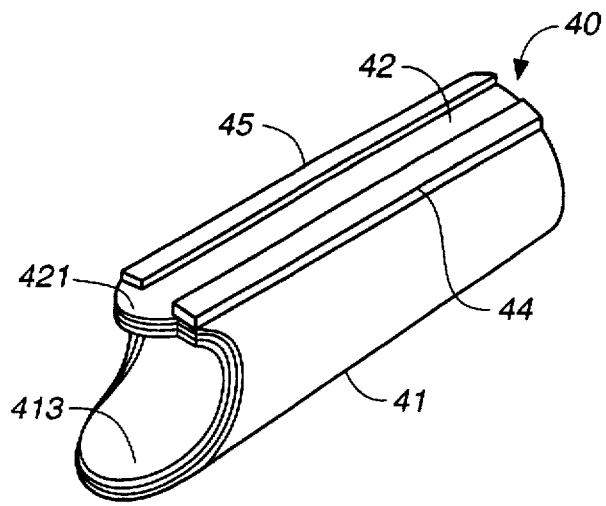
FIG._33A
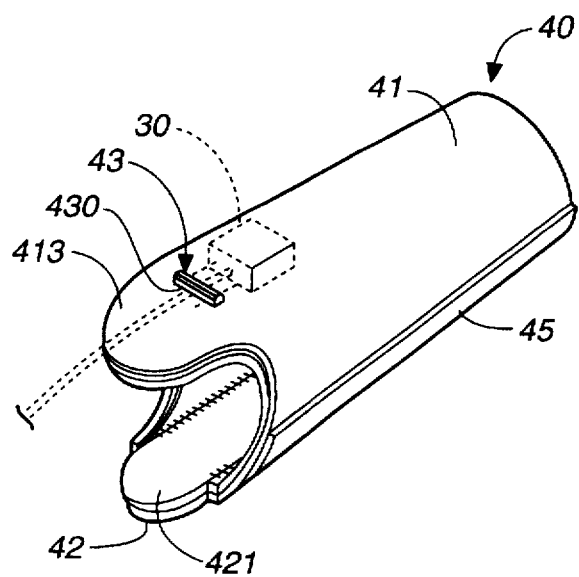
FIG._33B

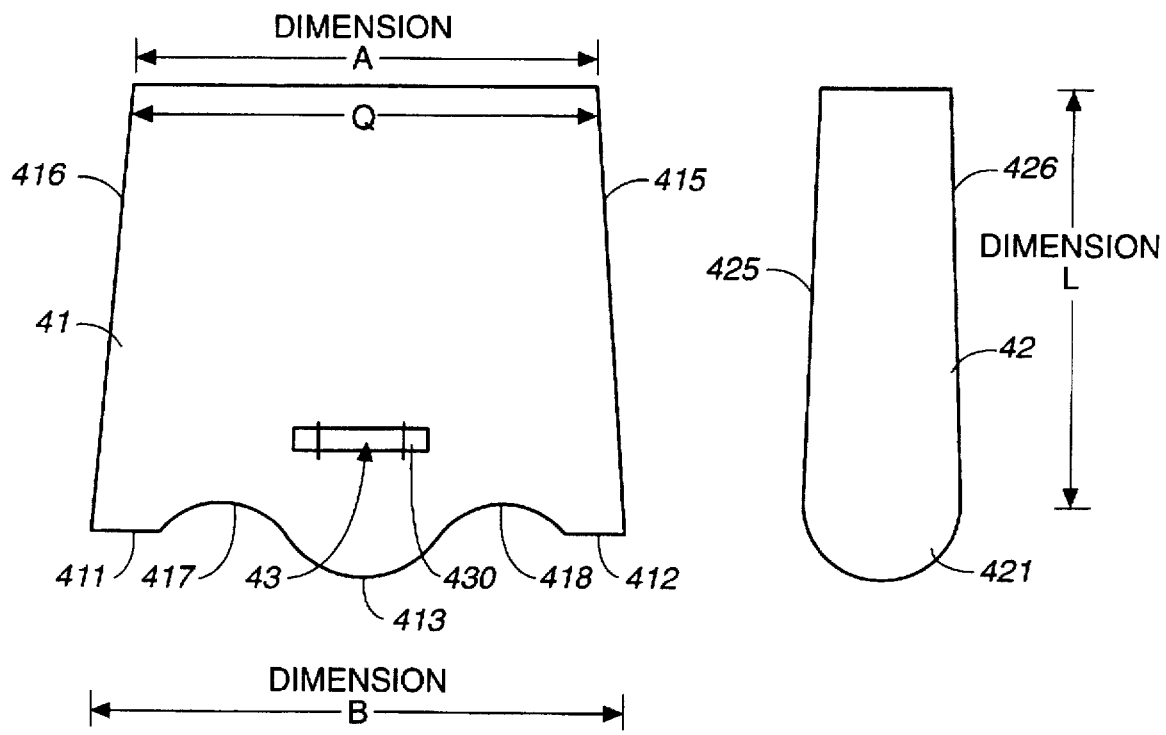
FIG._34A  FIG._34B
  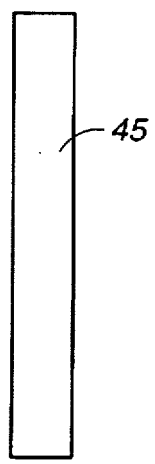
FIG._34C  FIG._34D

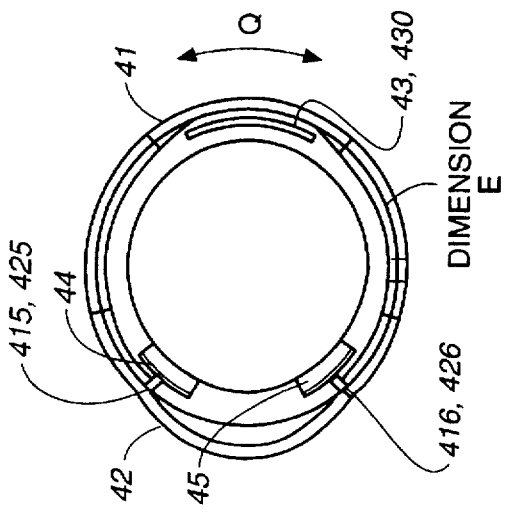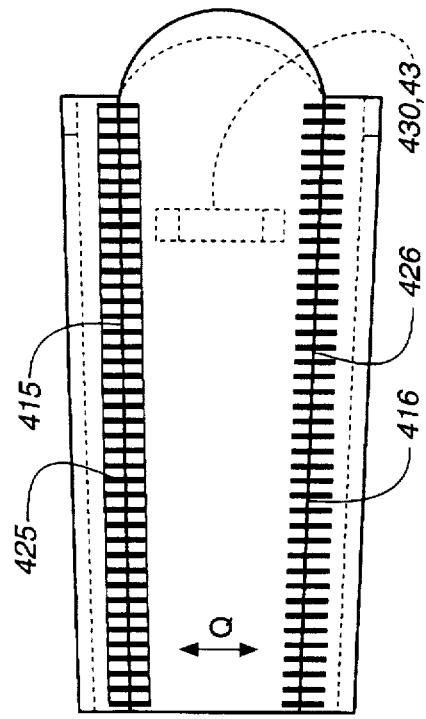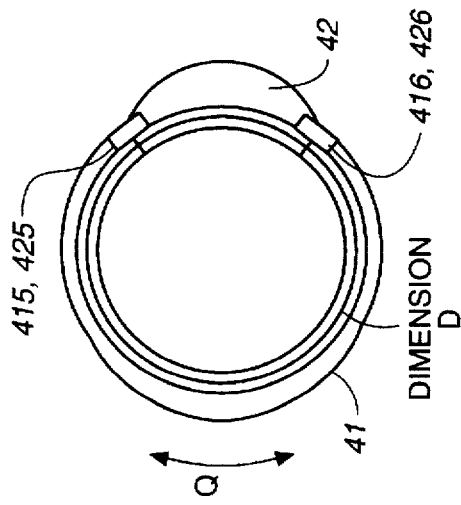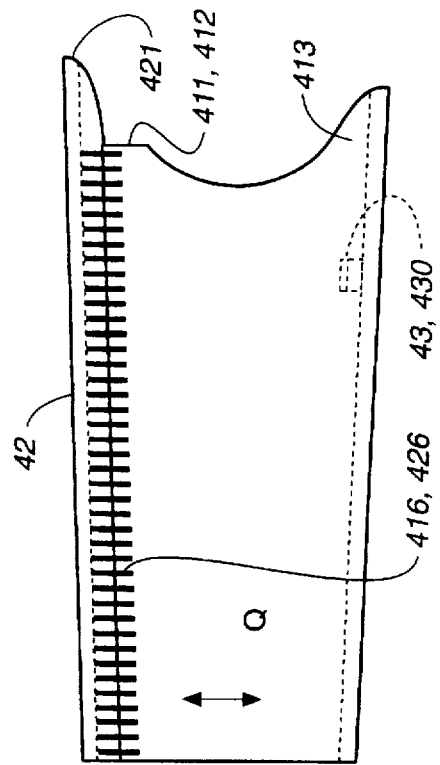

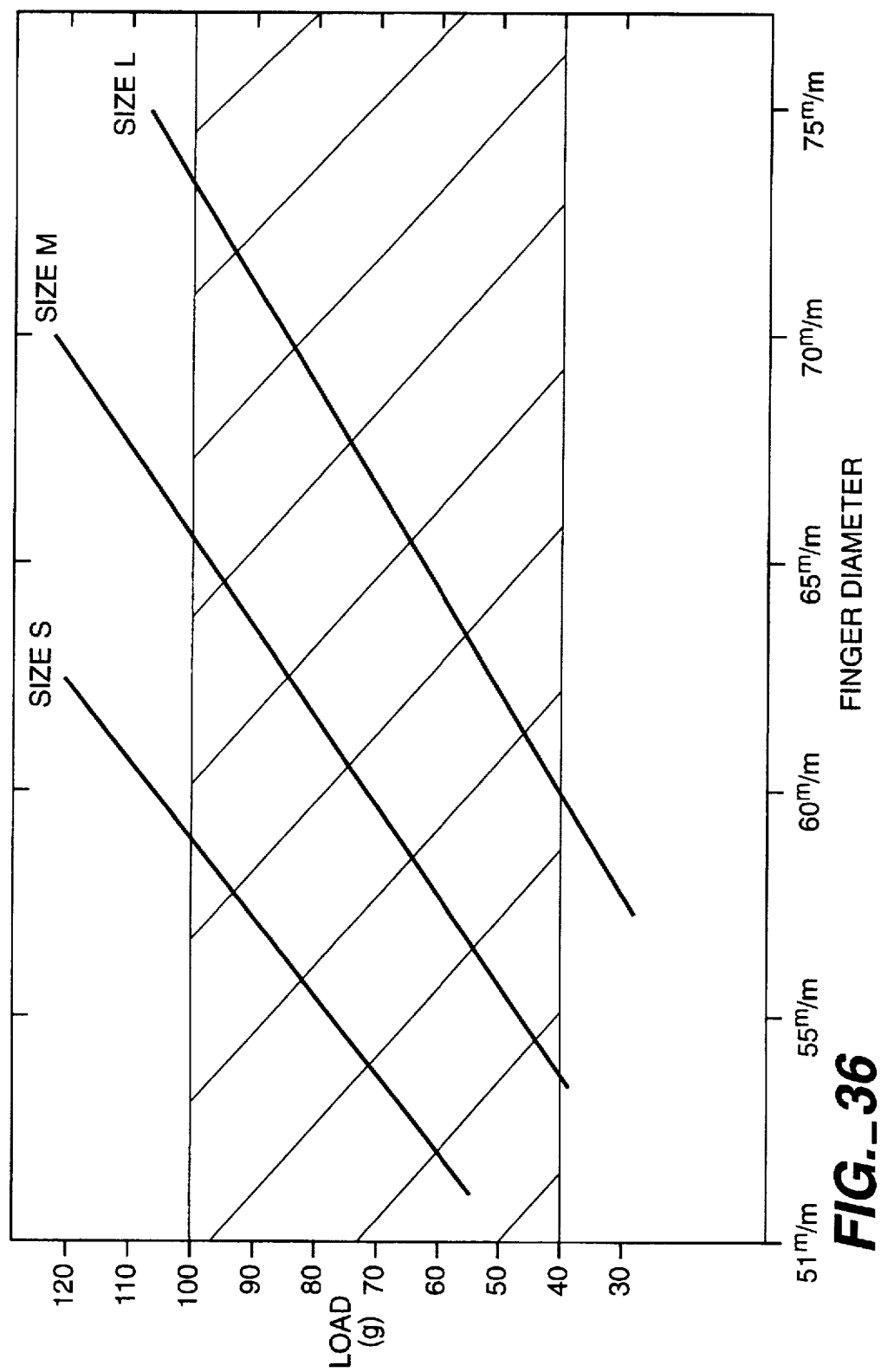
FIG._36

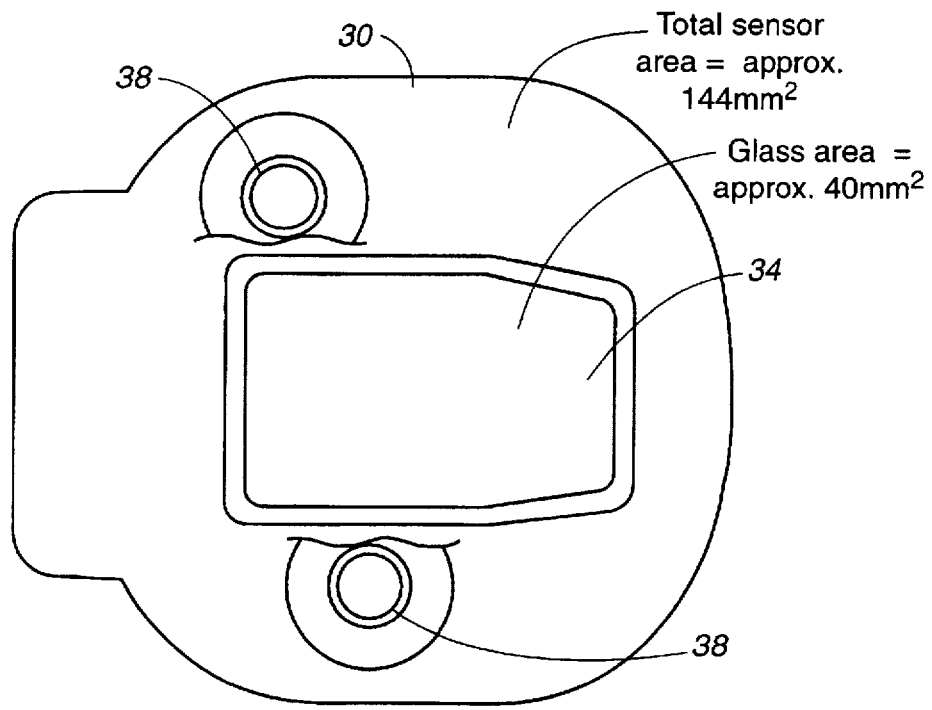
FIG._37
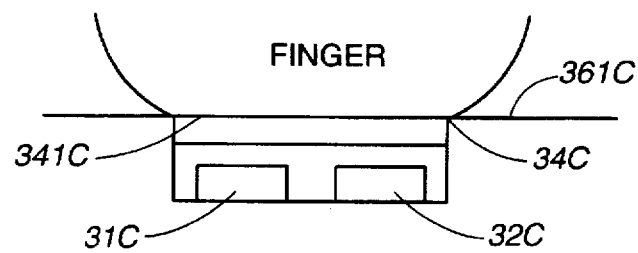
FIG._42A
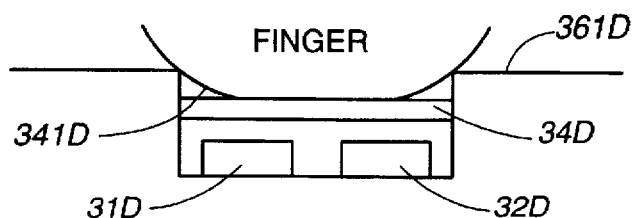
FIG._42B

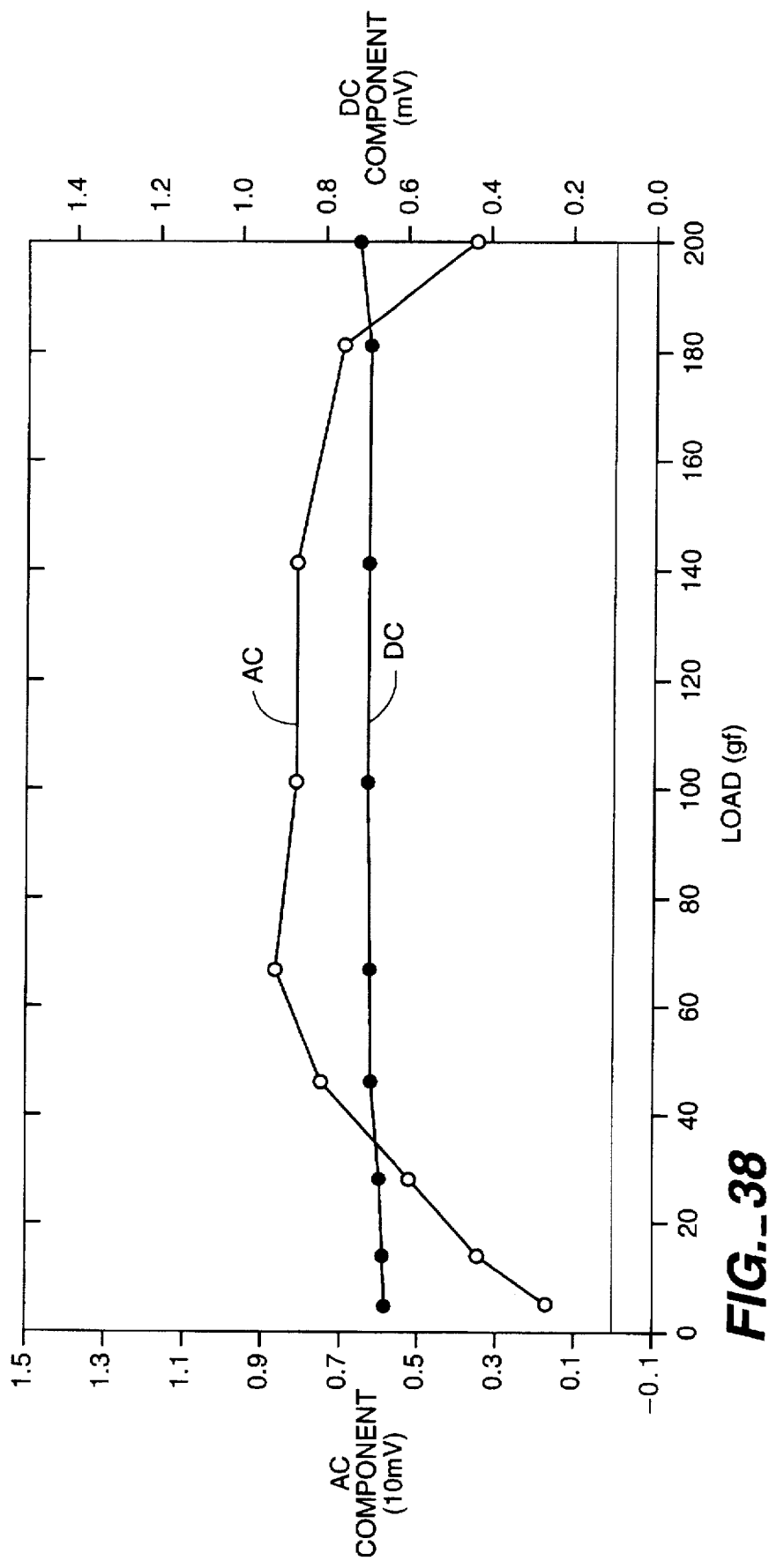
FIG._38

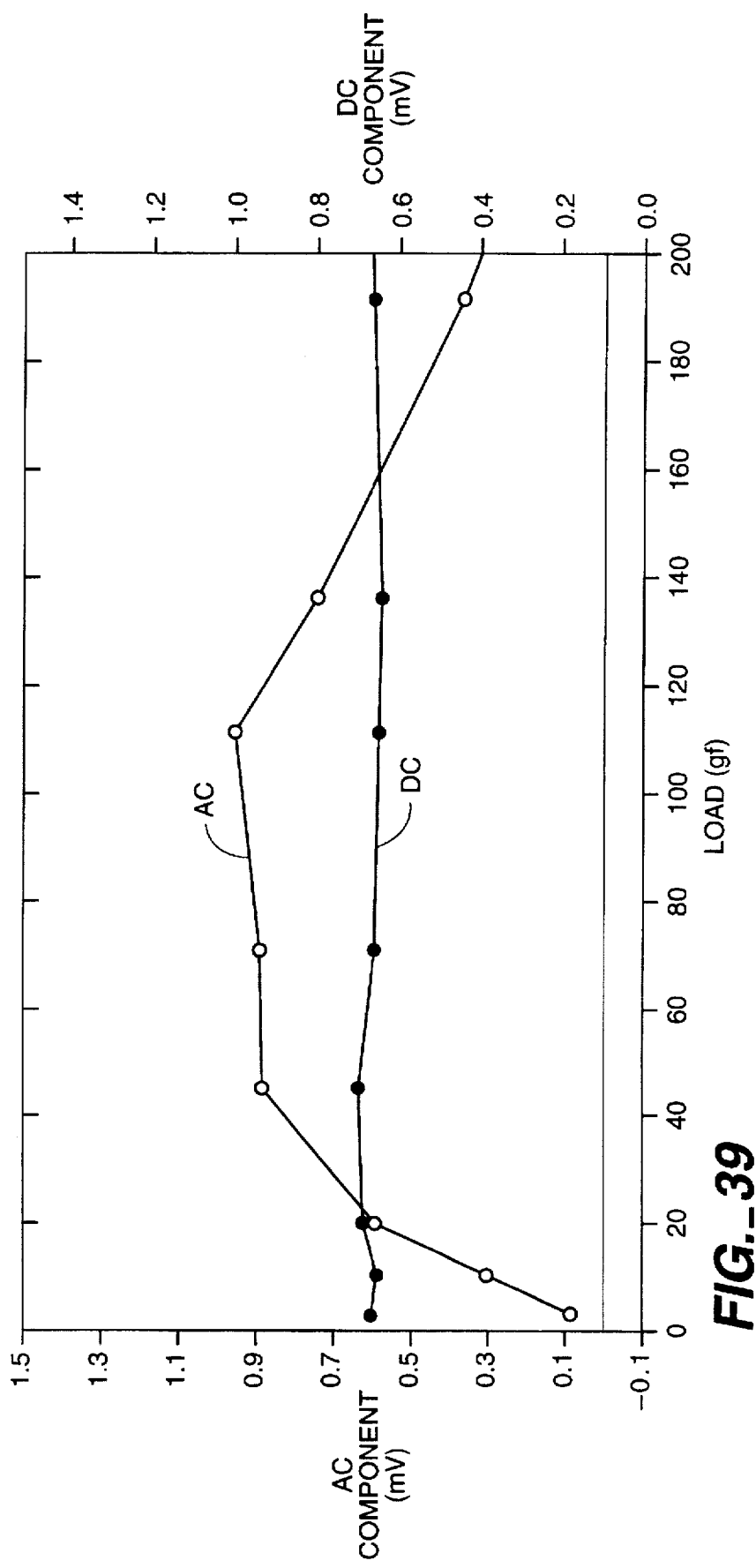
FIG._39

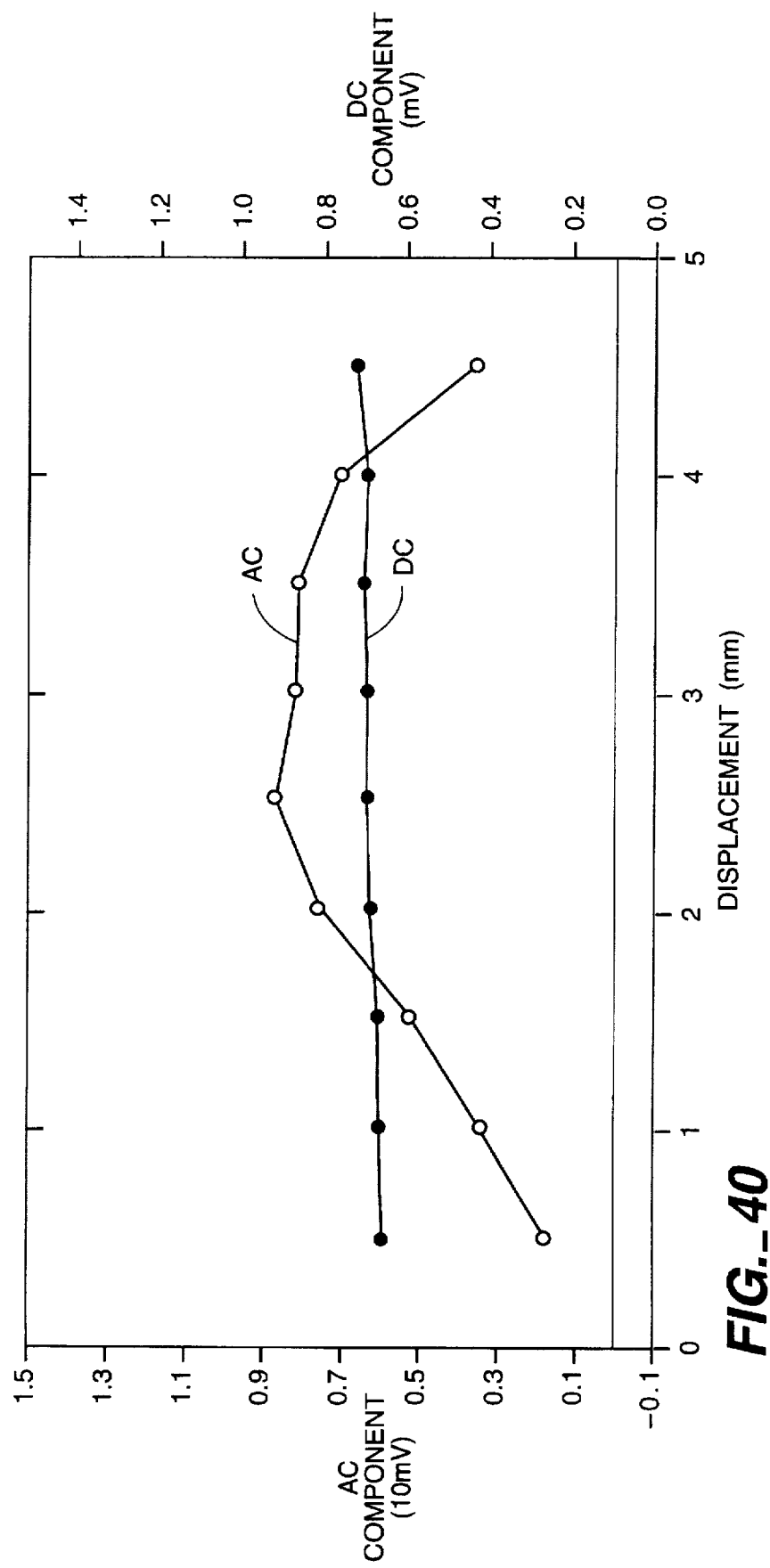
FIG._40

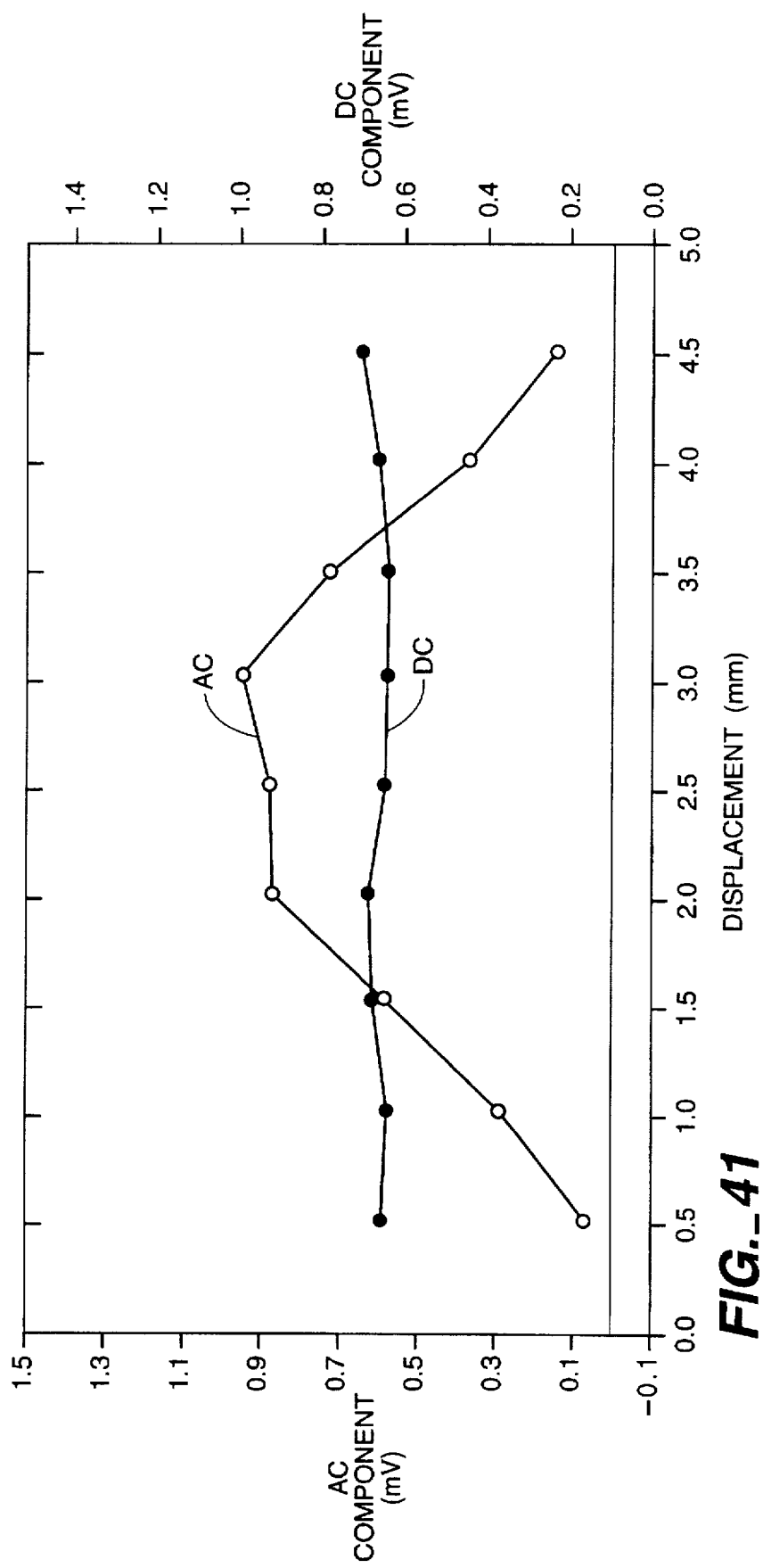
FIG._41

PULSE-WAVE MEASURING APPARATUS

BACKGROUND OF THE INVENTION

1. Field of the Invention

The present invention relates to a pulse wave measuring apparatus used to obtain the pulse rate, for example, by optically detecting a pulse signal. The invention more specifically relates to a structural technology for the pulse signal detection part of the pulse wave measuring apparatus.

2. Description of the Related Art

Optical devices are one type of pulse wave information measuring apparatus capable of measuring and displaying the pulse rate and other types of pulse wave information. Optical pulse wave measuring apparatuses typically expose the surface of a finger with light emitted from an LED, and detect the light reflected back from the blood vessels near the surface using, for example, a phototransistor to detect the change in reflected light quantity as representative of the change in blood volume. This detection result is then used to measure the pulse count and other parameters.

As shown in FIGS. 42A and 42B, light transmittance plates 34C and 34D are provided on the skin-surface side of LEDs 31C and 31D and phototransistors 32C and 32D with this type of pulse wave information measuring apparatus. The outside surface side 341C and 341D of the light transmittance plates 34C and 34D is then pressed against the finger to detect the pulse signal. If the surfaces surrounding light transmittance plates 34C and 34D are reference surfaces 361C and 361D, outside surfaces 341C and 341D of light transmittance plates 34C and 34D are either on the same plane as reference surfaces 361C and 361D or are recessed therefrom.

When a pulse wave detector thus constructed is assembled and used as the sensor unit, the sensor unit is held pressed against the skin by a surface fastening belt using a hook and loop-like material, such as Velcro®, similar to a conventional blood pressure gauge.

The problem with this design is that when the sensor unit is worn on the finger by pressing the sensor unit against the finger, wrapping a belt around the finger and sensor unit, and securing the belt with the surface fastener part thereof, the pressure applied between the sensor unit and finger must be adjusted by adjusting the belt tension each time the sensor unit is put on. This is because if the belt is too loose, external light may penetrate to the phototransistors through the gap between the belt and the finger. If this light reaches the sensor unit, it may not be possible to accurately measure the pulse signal.

Another problem with this method of securing the sensor unit with a surface fastener is that the force pressing the sensor unit against the finger varies each time the sensor unit is put on. As a result, the detection sensitivity tends to vary. It is therefore necessary when measuring the pulse rate to adjust the belt tension (tightness) and sensor-finger pressure by actually detecting the pulse signal to determine the fit obtaining optimum detection sensitivity. A certain amount of time and trouble is therefore required between preparing for pulse wave measurements and making the actual measurements.

Various sensor unit constructions were also studied by evaluating the detection sensitivity and data reliability. It was found that while disposing light transmittance plates 34C and 34D recessed from the reference surface 361D or on the same plane as the reference surface 361C is apparently more effective in terms of shielding the LED and phototransistor from external light, this structure in fact results in less contact with the finger. This then results in variations in the detection sensitivity.

OBJECTS OF THE INVENTION

Therefore it is an object of the present invention to overcome the aforementioned problems.

It is another object of the present invention to provide a pulse wave measuring apparatus capable of detecting the pulse signal with good sensitivity by enabling the sensor unit to be easily worn against the skin surface of, for example, the finger in a consistently stable condition.

SUMMARY OF THE INVENTION

To achieve a pulse wave measuring apparatus capable of detecting the pulse signal with good sensitivity by enabling the sensor unit to be easily worn against the skin surface of, for example, the finger in a consistently stable condition, a pulse wave measuring apparatus according to the present invention comprises a sensor unit comprising a light emitting element for emitting light to the finger, wrist, or other body surface, a receptor element for detecting the light emitted from the light emitting element and reflected back from the body surface, and a light transmittance plate disposed on the body surface side of the receptor element and light emitting element such that the outside surface of the light transmittance plate is pressed tight to the body surface. A main unit comprises a data processing means for obtaining such pulse information as the pulse count based on the pulse signal detection result supplied from the sensor unit. A sleeve-like sensor unit holding band is provided that is elastic in at least the circumferential direction, and is used to wear and hold the sensor unit against the body surface such that the light transmittance plate is tight to the body surface.

It should be noted that the body surfaces referenced herein shall not be limited to the surface of a finger or wrist, and may be any body surface, including the ankles or arm, where a pulse signal can be detected and the sensor unit can be held securely by means of a supporter-like sensor unit holding band.

Unlike the conventional method whereby the belt tightness must be adjusted with the surface fastener each time the sensor unit is put on, the sensor unit of the present invention can be pressed against the finger with appropriate force by simply fitting the sensor unit holding band to the finger if the sensor unit holding band has been sized appropriately to the finger because the sensor unit is held to a finger by means of a supporter-like sensor unit holding band with the pulse wave measuring apparatus according to the present invention. The method of the invention also prevents formation of gaps between the body surface and the sensor unit. The pulse signal detection sensitivity is therefore also consistently high.

If the outside surface of the sensor unit surrounding the light transmittance plate is the reference surface, it is preferable according to the present invention for the outside surface of the light transmittance plate to be exposed above this reference surface. Because the outside surface of the light transmittance plate covering the receptor element and light emitting element projects above that part of the sensor unit surrounding the light transmittance plate with this construction, the body surface is held tight to the entire outside surface of the light transmittance plate. This tight fit also remains stable when the body pressure against the light transmittance plate varies as a result of body movement.

In addition, because the outside surface of the light transmittance plate projects from the part surrounding the light transmittance plate, the contact area between the light transmittance plate and body surface can be assured to a certain degree, and the force pressing the sensor unit to the body surface can be easily controlled.

Moreover, residual blood in the blood vessels pressurized by the light transmittance plate is purged from that area when the light transmittance plate is pressed against the skin. As a result, the signal detected by the receptor element is minimally affected by residual blood in the blood vessels. The detection sensitivity of the pulse signal detected by the receptor element is therefore high, and the reliability of the obtained data is high. Less pressure between the light transmittance plate and body surface is thus needed to achieve consistently high sensitivity, and there is therefore less discomfort from wearing the sensor unit.

When the outside surface of the light transmittance plate is flat in the present invention, the body surface can be pressed evenly against the entire outside surface of the light transmittance plate.

When the outside surface of the light transmittance plate is a convex surface, pressure is applied to the light transmittance plate by simply holding the outside surface of the light transmittance plate lightly against the body surface, and positive contact between the body surface and outside surface of the light transmittance plate can therefore be improved.

A body ground terminal contacting the body surface when the light transmittance plate is tight to the body surface may also be provided according to the present invention on the outside surface of the sensor unit surrounding the light transmittance plate. The outside surface of the body ground terminal in this case preferably projects from the reference surface to a position lower than the outside surface of the light transmittance plate. When the skin is then pressed against the light transmittance plate, the body positively contacts the body ground terminal. The body ground terminal also does not inhibit tight contact between the body and the outside surface of the light transmittance plate because the outside surface of the body ground terminal is positioned lower than the outside surface of the light transmittance plate.

The sensor unit holding band in the present invention is preferably made from, for example, a material having a foam rubber layer, or from a material with a polyurethane layer. More specifically, if a thick material such as that used for diving wet suits and having a foam rubber layer or polyurethane layer is used for the sensor unit holding band, external light will not pass through the sensor unit holding band to the sensor unit even when the band is stretched to hold the sensor unit in place. Gaps will also not develop when the sensor unit holding band becomes wet because the dimensional stability of the band is good. It is therefore possible to stably detect the pulse signal without being affected by external light.

When the sensor unit holding band is made from a thick material having a foam rubber layer or polyurethane layer as described above, the band is preferably covered on both inside circumferential and outside circumferential surfaces with a stretchable fabric.

The inside and outside circumferential surfaces of the sensor unit holding band are also preferably covered with stretchable fabric of different colors. This makes it simple to identify the inside and outside of the sensor unit holding band.

The sensor unit holding band is further preferably manufactured from sheet-like strips fastened together at the edges thereof. The sensor unit holding band thus comprised does not result in unnecessary surface roughness, and is therefore more resistant to penetration by external light.

When the sensor unit holding band is manufactured from sheet-like strips fastened together at the edges thereof, a tape is preferably applied with adhesive to cover the seam between the edges of the strips. When this sensor unit holding band is then worn on the finger, there is no discomfort from the seam contacting the finger. Covering the seam with a tape helps to completely eliminate unevenness in the seam, thereby improving light-tightness and making the band more resistant to external light.

A sensor unit slipping prevention means preventing the position of the sensor unit from shifting inside the sensor unit holding band is also preferably disposed to the sensor unit holding band or sensor unit. The slipping prevention means keeps the sensor unit from shifting inside the sensor unit holding band and from falling out of the sensor unit holding band.

When, for example, the main unit and sensor unit are connected by a connector cable, the sensor unit slipping prevention means of the present invention may use an elastic body of which both ends are fastened to the inside circumference of the sensor unit holding band. Specifically, when the cable is passed between this elastic body and the inside circumference of the sensor unit holding band, the position of the sensor unit can be fixed by fastening with the elastic body that part of the cable near the connection between the cable and sensor unit.

The sensor unit slipping prevention means of the present invention may further use a protrusion provided on the sensor unit projecting in the direction opposite the light transmittance plate, and catching the inside circumferential surface of the sensor unit holding band.

The sensor unit holding band of the invention further preferably comprises a fingerhold extending in the lengthwise direction from the end of the band. It is therefore possible using the fingerhold to pull the sensor unit holding band on to the base of the finger, and the sensor unit holding band can be easily worn at the base of the finger even when the overall length of the sensor unit holding band itself is short.

The sensor unit holding band and sensor unit of the present invention are preferably comprised so that the load applied from the sensor unit to the body surface ranges from 1.0 gf/mm$^2$ to 2.8 gf/mm$^2$ per unit area of the light transmittance plate when the sensor unit is fixed to the body surface. The pulse signal detection sensitivity is high under these conditions because the force exerted by the sensor unit on the body surface is appropriate.

The sensor unit holding band and sensor unit in the present invention are preferably comprised to allow displacement between 2.0 mm and 3.0 mm from the position whereat the sensor unit is disposed without applying any load to the body surface, to the position whereat the light transmittance plate is fixed tight to the body surface by the sensor unit holding band. The pulse signal detection sensitivity is high under these conditions because the force exerted by the sensor unit on the body surface is appropriate.

The sensor unit holding band in this case is preferably manufactured from a material having a foam rubber layer or a material with a polyurethane layer.

A projection for focusing on the light transmittance plate the force of the sensor unit holding band pressing the sensor unit against the body surface is also preferably disposed on the side of the sensor unit opposite the light transmittance plate. When the projection is provided and the sensor unit is worn on the finger by the sensor unit holding band, the force of the sensor unit holding band pushing the sensor unit into the finger is focused on the light transmittance plate, thereby making it easier to regulate the load applied from the sensor unit to the body surface. It is therefore easier to design the sensor unit holding band and sensor unit to apply the optimum force from the sensor unit to the body surface.

If a wrist band for wearing the main unit on the wrist, and a cable connecting the main unit with the sensor unit, are further provided, a wristwatch-type pulse wave measuring apparatus that can be used to measure the pulse while running can also be provided according to the present invention.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts:

FIGS. 1A and B show the overall configuration and use of a pulse wave information measuring apparatus according to the first embodiment of the present invention;

FIG. 2 is a plan view of the main unit of the pulse wave measuring apparatus shown in FIGS. 1A and B;

FIG. 3 is a side view showing of the main unit of the pulse wave measuring apparatus shown in FIGS. 1A and B from the three o'clock direction of a wristwatch;

FIG. 4 is a plan view of the sensor unit used in the pulse wave measuring apparatus shown in FIGS. 1A and B;

FIG. 5 is a cross-sectional view taken along line I—I' in FIG. 4;

FIG. 6 is a cross-sectional view taken along line II—II' in FIG. 4;

FIG. 7 is a cross-sectional view taken along line III—III' in FIG. 4;

FIG. 8 is a graph showing the emissions spectrum of an InGaN blue LED used in the pulse wave measuring device apparatus in FIGS. 1A and B;

FIG. 9 is a graph of the light reception characteristics of an InGaP phototransistor used in the pulse wave measuring device apparatus in FIGS. 1A and B;

FIG. 10 is a graph of the light reception characteristics of a filtered phototransistor unit used in the pulse wave measuring device apparatus in FIGS. 1A and B;

FIG. 11 illustrates the operation of the sensor unit in the pulse wave measuring device apparatus in FIGS. 1A and B when worn on a finger;

FIG. 12 is a functional block diagram of the data processing circuit used in the pulse wave measuring apparatus shown in FIGS. 1A and B;

FIG. 13 is a schematic diagram of electrical connections of a connector in the pulse wave measuring apparatus shown in FIGS. 1A and B;

FIGS. 14A and B are diagrams of the connector piece used in the connecting means of the pulse wave measuring apparatus shown in FIGS. 1A and B;

FIG. 15 is a diagram of the connector used in the connecting means of the pulse wave measuring apparatus shown in FIGS. 1A and B;

FIG. 16 is a cross-sectional view showing the connector piece shown in FIGS. 14A and B mounted on the connector shown in FIG. 15;

FIG. 17A is a graph of the relationship between optical wavelength and the optical transmittance of the skin, and FIG. 17B shows the relationship between optical wavelength and the light absorbance of various types of hemoglobin;

FIG. 18 is a graph showing the emissions spectrum of a GaP LED that can be used in the pulse wave measuring apparatus in FIGS. 1A and B;

FIG. 19 is a graph of the light reception characteristics of a GaAsP phototransistor used in the pulse wave measuring apparatus in FIGS. 1A and B;

FIGS. 20A-1, 20A-2, 20B-1, and 20B-2 illustrate the effect of improving contact between the finger and light transmittance plate in the sensor unit used in the pulse wave measuring apparatus in FIGS. 1A and B;

FIGS. 21A–21B illustrate the effect of reducing the effects of residual blood on the signal detected by the phototransistor in a sensor unit used in the pulse wave measuring apparatus in FIGS. 1A and B;

FIG. 22 is a graph of the evaluation results of the relationship between the sensor unit pressure on the finger and the levels of the AC signal and DC signal detected by the phototransistor in a pulse wave measuring apparatus as shown in FIGS. 1A and B in which the light transmittance plate is recessed from the reference surface 0.2 mm for comparison;

FIG. 23 is another graph of the evaluation results (the relationship between the sensor unit pressure on the finger and the levels of the AC signal and DC signal detected by the phototransistor) shown in FIG. 22 obtained in a separate test under the same basic conditions using a pulse wave measuring apparatus as shown in FIGS. 1A and B in which the light transmittance plate is recessed from the reference surface 0.2 mm for comparison;

FIG. 24 is a graph of the relationship obtained from the results shown in FIG. 22 between the sensor unit pressure on the finger and the ratio of the AC signal to DC signal detected by the phototransistor.;

FIG. 25 is a graph of the evaluation results of the relationship between the sensor unit pressure on the finger and the levels of the AC signal and DC signal detected by the phototransistor in a pulse wave measuring apparatus as shown in FIGS. 1A and B in which the light transmittance plate projects 0.25 mm from the reference surface according to the preferred embodiment;

FIG. 26 is another graph of the evaluation results (the relationship between the sensor unit pressure on the finger and the levels of the AC signal and DC signal detected by the phototransistor) shown in FIG. 25 obtained in a separate test under the same basic conditions using a pulse wave measuring apparatus as shown in FIGS. 1A and B in which the light transmittance plate projects 0.25 mm from the reference surface according to the preferred embodiment;

FIG. 27 is a graph of the relationship obtained from the results shown in FIG. 25 between the sensor unit pressure on the finger and the ratio of the AC signal to DC signal detected by the phototransistor;

FIG. 28 is a cross-sectional view of a separate sensor unit that can be used in the pulse wave measuring apparatus shown in FIGS. 1A and B;

FIG. 29 is a cross-sectional view taken along line I—I' in FIG. 4 of the sensor unit used in a pulse wave measuring apparatus in accordance with a second embodiment of the present invention;

FIG. 30 is a cross-sectional view taken along line II—II' in FIG. 4 of the sensor unit used in a pulse wave measuring apparatus in accordance with the second embodiment of the invention;

FIG. 31 is a cross-sectional view taken along line III—III' in FIG. 4 of the sensor unit used in a pulse wave measuring apparatus in accordance with the second embodiment of the invention;

FIG. 32A is a perspective view of the sensor unit holding band used in a pulse wave measuring apparatus according to the second embodiment of the invention, and FIG. 32B is a perspective view of the sensor unit holding band when viewed from an upside down position;

FIG. 33A is a perspective view of the sensor unit holding band shown in FIGS. 32A and 32B inverted from the condition shown in FIG. 32A, and FIG. 33B is a perspective view of the sensor unit holding band shown in FIGS. 32A and 32B inverted from the condition shown in FIG. 32B;

FIGS. 34A–34D are plan views of the sheet-like strips from which the sensor unit holding band shown in FIGS. 32A and 32B is manufactured;

FIG. 35A is a rear view of the sensor unit holding band shown in FIGS. 32A and 32B, FIG. 35B is a left side view thereof, FIG. 35C is a plan view thereof, and FIG. 35D is a front view thereof;

FIG. 36 is a graph of the finger (ring) size and the load applied from the sensor unit to the finger surface when the sensor unit shown in FIGS. 29–31 is worn on the finger using the sensor unit holding band shown in FIGS. 32A and 32B;

FIG. 37 illustrates the part of the finger surface contacted by the sensor unit shown in FIGS. 29–31, and the specific contact area;

FIG. 38 is a graph of the relationship between the pulse signal detection sensitivity and the pressure of the sensor unit against the finger surface in accordance with a sensor unit as shown in FIGS. 29–31;

FIG. 39 is a graph of a different relationship between the pulse signal detection sensitivity and the pressure of the sensor unit against the finger surface measured with the same method as that used to obtain the results shown in FIG. 38;

FIG. 40 is a graph of the relationship between the pulse signal detection sensitivity and the sensor unit displacement when a sensor unit as shown in FIGS. 29–31 is pressed against the finger surface;

FIG. 41 is a graph of a different relationship between the pulse signal detection sensitivity and the sensor unit displacement measured with the same method as that used to obtain the results shown in FIG. 40 when a sensor unit as shown in FIGS. 29–31 is pressed against the finger surface; and FIG. 42A is a cross-sectional view of the sensor unit used in a conventional pulse wave information measuring apparatus, and FIG. 42B is a similar cross-sectional view of a different conventional sensor unit.

DESCRIPTION OF THE PREFERRED EMBODIMENTS

The preferred embodiments of the present invention are described below with reference to the accompanying figures.

Embodiment 1

Overall Configuration

FIGS. 1A and B shows the overall configuration and use of a pulse wave information measuring apparatus according to the first embodiment of the invention.

In FIGS. 1A and B, pulse wave measuring device 1 (such as, wristwatch-type pulse wave measuring apparatus pulsimeter) according to the present embodiment comprises a main unit 10 having a wristwatch construction, cable 20 connected to main unit 10, and sensor unit 30 (pulse signal detector) provided on the end of cable 20. Wrist band 12, enabling main unit 10 to be worn freely on the arm, is operatively coupled to main unit 10 for wrapping around the arm from the direction of twelve o'clock on the wristwatch and being fastened in the direction of six o'clock. Sensor unit 30 is held by sleeve-like sensor unit holding band 40 (sensor unit holding means) on the index finger (body) between the knuckle and first joint. Covering the finger in this area prevents gaps from developing between sensor unit 30 and the finger, and depending upon the material used for sensor unit 30 permits the finger to bend easily.

Sensor Unit Holding Band

A thick material, such as that used for diving wet suits, is preferably employed as sensor unit holding band 40 in the present embodiment. This material is a compound material comprising a synthetic jersey or other stretch fabric applied to both front and back of the foamed rubber core layer (e.g., a polyurethane rubber layer). This imparts an appropriate elasticity to the sensor unit holding band 40, particularly in the circumferential direction. Unlike other methods holding the sensor unit with a surface fastener, gaps between the finger and sensor unit holding band 40 can be prevented by simply selecting a sleeve-like sensor unit holding band 40 according to the size of the user's finger.

When a sleeve-like sensor unit holding band 40 is used, sensor unit 30 can be pressed against the finger with a constant pressure, and detection sensitivity is therefore high, by simply selecting a sensor unit holding band 40 sized appropriately to the finger on which it is worn.

In other words, the pulse signal detection sensitivity is high when the pressure holding sensor unit 30 against the finger surface is within an appropriate range, and tends to drop when the pressure is above or below this appropriate range. With the sleeve-like sensor unit holding band 40 of the present invention, however, a constant appropriate pressure is applied by simply wearing the sensor unit holding band 40 on the finger, and detection sensitivity is therefore high. After sensor unit 30 is mounted on the finger using sensor unit holding band 40, pulse signals can be detected with high sensitivity by simply confirming the fit, and there is no noticeable delay between preparing for pulse count measurements and the start of actual measurements.

Configuration of the Main Unit

FIG. 2 is a plan view of the main unit of the pulse wave measuring apparatus according to the present embodiment with the wrist band and cable removed, and FIG. 3 is a side view of the pulse wave measuring apparatus from the three o'clock direction of a wristwatch.

As shown in FIG. 2, main unit 10 comprises a resin watch case 11 (main case) with a liquid crystal display device 13 (display) on the top side of this watch case 11. Display device 13 is used to digitally display the pulse count and other pulse information in addition to the current time and date.

Data processing circuit 50, which is used to process the detection signals to display on LCD 13 the change in pulse count, for example, based on the detection result (pulse signal) returned by sensor unit 30, is built in to watch case 11. A stopwatch circuit is also built in to data processing circuit 50, enabling the normal time, lap time, split time, and other time information to be displayed on LCD 13.

Button switches 111–115 used to select the various operating modes, including setting the time and display mode, are also provided on the outside of watch case 11. Button switches 116 and 117 are also provided on the surface of watch case 11. The power supply for pulse wave information measuring apparatus 1 is button-type battery 59 housed inside watch case 11. Cable 20 supplies power from battery 59 to sensor unit 30, and inputs the detection results from sensor unit 30 to data processing circuit 50 inside watch case 11.

As the functions of pulse wave information measuring apparatus 1 are increased, it is also necessary to enlarge main unit 10, but because of the limitations imposed by main unit 10 being worn on the arm, main unit 10 cannot be enlarged in the directions of six o'clock and twelve o'clock. A horizontally long watch case 11 in which the length in the direction of three o'clock and nine o'clock is greater than the length in the direction of six o'clock and twelve o'clock is therefore used for main unit 10 in the present embodiment.

Wrist band 12 is therefore connected to watch case 11 at a position offset toward the three o'clock position. As a result, main unit 10 has a large protrusion 101 in the direction of nine o'clock when viewed from the wrist band 12, but does not have a similarly large protrusion in the three o'clock direction. As a result, the wrist can be bent with relative freedom and comfort even though the watch case 11 is long from side to side, and the back of the hand will also not strike the watch case 11 when, for example, the user falls and the hand is bent back because there is no large projection in the direction of three o'clock.

Using the wide side-to-side construction of watch case 11, flat piezoelectric device 58 used for a buzzer is disposed to the nine o'clock side of battery 59. The center of gravity of main unit 10 is therefore offset in the direction of three o'clock because battery 59 is heavier than piezoelectric device 58.

Wrist band 12 is therefore also attached closer to the true center of gravity, and can thereby hold main unit 10 stably on the arm.

The thickness of main unit 10 can also be reduced because battery 59 and flat piezoelectric device 58 are disposed side by side in the planar direction. This arrangement also enables the user to easily replace battery 59 if battery cover 118 is provided on back cover 119.

Structure Stopping the Main Unit from Rotating Around the Wrist

Referring to FIG. 3, a connecting member 105 for holding the holding pin 121 attached to the end of wrist band 12 is formed on the outside of watch case 11 at the twelve o'clock position. A holder 106 is formed on the outside of watch case 11 at the six o'clock position, and a fastener 122 is attached to holder 106; wrist band 12 is wrapped around the wrist and folded back around fastener 122 at some intermediate lengthwise position, and held by fastener 122. Turning stop 108 forming an approximately 115° angle to back 119 is formed integrally to watch case 11 extending from the edge of flat back 119 to holder 106 at the six o'clock position of main unit 10. As a result, when pulse wave information measuring apparatus 1 is worn and held on the top L1 (the same side as the back of the hand) of the left wrist L (arm), back 119 of watch case 11 is tight against top L1 of wrist L, and turning stop 108 is touching side L2 on the same side of the arm as the radius R. In this position, back 119 of main unit 10 straddles the radius R and ulna U of the arm, and the curved part 109 between turning stop 108 and back 119 is pressed against the radius R of the arm. Because turning stop 108 and back 119 form an anatomically ideal angle of approximately 115°, attempts to turn main unit 10 in the direction of arrow A or arrow B are stopped, and main unit 10 will not turn further.

Note that rotation around the wrist is prevented at only two places on one side by back 119 and turning stop 108. As a result, rotation is effectively prevented even when the arm is thin because back 119 and turning stop 108 reliably contact the arm, and there is no constricted feeling when the arm is thick.

Sensor Unit Configuration

FIG. 4 is a plan view of the sensor unit used in the pulse wave measuring apparatus shown in FIG. 1; FIG. 5 is a cross-sectional view taken along line I—I' in FIG. 4; FIG. 6 is a cross-sectional view taken along line II—II' in FIG. 4; and FIG. 7 is a cross-sectional view taken along line III—III' in FIG. 4.

Referring to FIGS. 4 and 5, sensor unit 30 comprises component housing 300 inside sensor frame 36, which is used as the sensor unit casing, and circuit board 35 is disposed inside component housing 300. LED 31, phototransistor 32, diode 391, transistor 392, and other electronic components are mounted on circuit board 35. Bushing 393 fastens the end of cable 20 in sensor unit 30, and the various leads in cable 20 are soldered to the appropriate parts of the circuit pattern formed on circuit board 35. Note that sensor unit 30 is worn at the base of the finger oriented such that cable 20 leads from the base of the finger to main unit 10. LED 31 and phototransistor 32 are therefore disposed lengthwise to the finger with LED 31 towards the fingertip and phototransistor 32 towards the base of the finger.

As shown in FIG. 5, the back of component housing 300 is covered by back cover 302 covering the back of sensor frame 36. A transparent window is formed on the top of sensor frame 36 (the actual pulse signal detector) by means of light transmittance plate 34, which is a glass plate. Circuit board 35 is fixed inside component housing 300 opposing light transmittance plate 34. As a result, the light emitting face and receptor face, respectively, of LED 31 and phototransistor 32 are facing light transmittance plate 34. As a result, when outside surface 341 (the finger contact surface, i.e., sensor surface) of light transmittance plate 34 contacts the finger and LED 31 emits to the finger, phototransistor 32 can detect the emitted light that is reflected back from the finger.

As shown in FIGS. 5, 6, and 7, outside surface 341 of light transmittance plate 34 projects above the reference surface, which as used herein refers to the outside surface 361 of sensor frame 36 surrounding light transmittance plate 34.

As shown in FIG. 6, two body ground terminals 38 are fixed in sensor frame 36 by screws 306 on opposing sides of light transmittance plate 34. These body ground terminals 38 contact the finger surface when light transmittance plate 34 is worn against the finger. Note further that packing 394 is fit around body ground terminals 38.

As also shown in FIG. 6, body ground terminals 38 project above the reference surface (outside surface 361 of sensor frame 36). However, outside surfaces 381 of body ground terminals 38 (i.e., the finger contact surfaces) are positioned lower than outside surface 341 of light transmittance plate 34, i.e., are positioned at a height between the reference surface and the outside surface 341 of light transmittance plate 34.

An InGaN (indium-gallium-nitrogen) blue LED is, for example, used for LED 31 in this embodiment. The emissions spectrum of this type of LED has an emissions peak at 450 nm as shown in FIG. 8, and an emissions wavelength range from 350 nm to 600 nm. Corresponding to the emissions characteristics of LED 31, a GaAsP (gallium-arsenic-phosphorus) phototransistor is used as phototransistor 32 in this embodiment; the detection range of this element has a primary sensitivity range from 300 nm to 600 nm with sensitivity also extending below 300 nm as shown in FIG. 9.

It is also possible to use a sensor unit adding a filter to this element as phototransistor 32. The primary sensitivity range of the detection range of such a sensor unit is from 400 nm to 550 nm as shown in FIG. 10 by way of example.

When sensor unit 30 thus comprised is worn at the base of the finger as shown in FIG. 11 by means of sensor unit holding band 40 (not shown in the figure), LED 31 and phototransistor 32 are positioned with the light emitting and detection surfaces thereof facing the skin surface. When LED 31 emits toward the finger, the light reflected from the body (blood vessels) is detected by phototransistor 32, the detection result (pulse signal) is output from phototransistor 32 to main unit 10 via cable 20, and the pulse count can then be determined from the pulse signal by main unit 10.

Configuration of the Data Processing Circuit

FIG. 12 is a functional block diagram of portions of the functions of the data processing circuit in the watch case. In this arrangement, pulse signal converter 51 of data processing circuit 50 converts the signal input from sensor unit 30 by cable 20 to a digital signal, and outputs the digital signal to pulse signal memory 52. Pulse signal memory 52 is, for example, a random access memory or RAM for storing the pulse data after conversion to digital signals. Pulse signal calculator 53 reads and performs frequency analysis (by means of, for example, a high speed Fourier transform operation) the signal stored to pulse signal memory 52, and inputs the result to pulse component extractor 54. Pulse component extractor 54 extracts the pulse component from the input signal from pulse signal calculator 53, and outputs to pulse rate calculator 55. Pulse rate calculator 55 calculates the pulse count based on the input pulse wave frequency component, and outputs the result to LCD 13.

Structure for Connecting the Cable and Main Unit

So that pulse wave information measuring apparatus 1 according to the present embodiment can normally be used as a common wristwatch, cable 20 can be connected and disconnected at the side of main unit 10 near the six o'clock position as shown in FIG. 1A. More specifically, a connector 70 is formed on the outside surface of the part extended as turning stop 108 at the six o'clock position on the edge of main unit 10 such that connector piece 80 disposed on the end of cable 20 can be fit thereto as shown in FIG. 3. Connector 70 is therefore at the front when seen by the user with main unit 10 worn on the arm, and operation is therefore simple. The user can also freely bend the wrist while running, and the back of the hand will not strike connector 70 even if the user falls while running, because connector 70 does not project at the three o'clock position from main unit 10.

The electrical connections completed between connector 70 and connector piece 80 (connector means) are as shown in FIG. 13.

Referring to FIG. 13, terminals 751–756 (first terminal group) are disposed on connector 70, which is provided on the main unit 10, and electrodes 831–836 (second terminal group) corresponding to these terminals 751–756 are disposed to connector piece 80.

Terminal 752 is a positive terminal for supplying second drive voltage VDD to LED 31 through electrode 832; terminal 753 is a terminal set to the negative potential of LED 31 through electrode 833; terminal 754 is provided for supplying the constant drive voltage VREG to the collector terminal of phototransistor 32 through electrode 834; terminal 751 is the terminal to which the signal from the emitter terminal of phototransistor 32 is input through electrode 831; and terminal 755 is the terminal to which is input through electrode 835 the signal for detecting whether connector piece 80 is connected to connector 70.

Electrode 836 grounds sensor unit 30 to the body via body ground terminals 38 shown in FIGS. 4 and 6, and shields electrodes 831–836 by dropping VDD to the ground when terminal 756 and electrode 836 are electrically connected.

A first capacitor C1 and first switch SW1 are inserted between the LED 31 terminals (between electrodes 832 and 833) in connector piece 80. This switch SW1 is closed when connector piece 80 is disconnected from connector 70, connecting first capacitor C1 parallel to LED 31, and is open when connector piece 80 is connected to connector 70. A second capacitor C2 and second switch SW2 are similarly inserted between the terminals (electrodes 831 and 834) of phototransistor 32. This switch SW2 is closed when connector piece 80 is disconnected from connector 70, connecting the second capacitor C2 parallel to phototransistor 32, and is open when connector piece 80 is connected to connector 70.

The structure of connector piece 80 and connector 70 is described further below with reference to FIGS. 14A–16.

FIGS. 14A and B are enlarged views showing the construction of the connector piece disposed at the end of the cable, FIG. 15 is an enlarged view of the connector on the main unit, and FIG. 16 is a vertical cross-sectional view showing the connector piece connected to the connector.

Referring to FIGS. 14A and B, a pair of projections 81 and 82 projecting downward is formed on both sides of the bottom 801 of connector piece 80. Four engaging members 811, 812, 821, and 822 (second group of engaging claws) project toward the inside at the bottoms of these projections 81 and 82.

Six electrodes 831, 832, 833, 834, 835, 836 (second terminal group) are formed on the bottom 801 of connector piece 80, and an annular ridge member 841, 842, 843, 844, 845, and 846 are formed around each electrode. As will be described in more detail below, connector piece 80 is thus fit down over connector 70 and then slid in the direction of arrow Q to mount connector piece 80 on connector 70 with electrodes 831–836 formed in two rows of electrodes 831, 833, and 833, and electrodes 834, 835, and 836 in this sliding direction (the direction of arrow Q). In addition, the electrodes 831–836 in each row are arranged at an angle offset in a direction intersecting the sliding direction (direction of arrow Q) of connector piece 80.

Two operating pins 837 and 838 for switching a circuit blocking the effects of static electricity when cable 20 is connected to main unit 10 are also provided on the bottom of connector piece 80. The ends of these operating pins 837 and 838 project from bottom 801 of connector piece 80 when connector piece 80 is removed from connector 70.

As shown in FIG. 15, engaging parts 71, 72, 73, and 74 (first group of engaging claws) projecting to the outside are formed on connector 70. Therefore, if, after fitting connector piece 80 down over connector 70 such that projections 81 and 82 of connector piece 80 are positioned outside engaging parts 71, 72, 73, and 74 of connector 70, and engaging members 811 and 821 of connector piece 80 are positioned between engaging parts 71 and 72 and engaging parts 73 and 74, respectively, connector piece 80 is pushed towards connector 70 such that engaging members 811 and 821 pass between engaging parts 71 and 72 and engaging parts 73 and 74, respectively, and connector piece 80 is then slid in the direction of arrow Q, engaging members 811, 821 become seated below engaging parts 71 and 73.

Engaging members 812 and 822 are also seated below engaging parts 72 and 74.

As a result, engaging members 811, 821, 812, and 822 hold engaging parts 71, 72, 73, and 74 between engaging members 811, 821, 812, and 822 and bottom 801 of connector piece 80, and connector piece 80 can be easily and reliably connected to connector 70.

Engaging mechanism 700 is thus comprised such that connector piece 80 is engaged when connector piece 80 is slid across connector 70 in the direction of arrow Q, and this engaged state is released when connector piece 80 is slid from this state in the opposite direction (the direction of arrow R). The engaging mechanism thus comprised reliably engages even while using few parts.

When connector piece 80 is slid from six o'clock in the direction of twelve o'clock on connector 70, the force applied to main unit 10 is applied in the direction whereby rotation of main unit 10 is made difficult by turning stop 108. Because main unit 10 therefore does not turn around the wrist even when connector piece 80 is mounted, mounting is simple.

It should be noted that terminals 751–756, like electrodes 831–836, are formed in two rows of terminals 751, 752, and 753 and terminals 754, 755, and 756 in the sliding direction of connector piece 80 (the direction of arrow Q). Each of these rows of terminals 751–756 is, like electrodes 831–836, arranged at an angle offset in a direction intersecting the sliding direction (direction of arrow Q) of connector piece 80. Therefore, when connector piece 80 is mounted on connector 70, the six terminals 751–756 are electrically connected to the six electrodes 831–836, respectively, and the measurement result from sensor unit 30 can be input to main unit 10 through cable 20.

It should be noted that because terminals 751–756 and electrodes 831–836 are arrayed in two rows in the sliding direction of connector piece 80, and the positions between each of the terminals and each of the electrodes are diagonally offset in a direction intersecting this sliding direction, non-corresponding terminals 751–756 and electrodes 831–836 will not contact even when connector piece 80 is slid across connector 70. Moreover, because the terminals and electrodes can be separated from each other even when the area of connector 70 is confined, shorting between terminals and between electrodes does not easily occur even if water penetrates between connector piece 80 and connector 70. Furthermore, tracking between different-potential terminals and electrodes does not occur because terminals 752, 754, and 756, and electrodes 832, 834, and 836 to which the drive voltage is applied are specifically arrayed at separated positions.

Stopper Mechanism Construction

As will be known from FIG. 15, vertical faces 711, 721, 731, and 741 are formed on engaging parts 71–74 on the side in the direction of arrow Q. Therefore, if connector piece 80 is slid in the direction of arrow Q (second operation) when mounting connector piece 80 on connector 70, engaging members 811, 812, 821, and 822 respectively contact vertical faces 711, 721, 731, and 741, thus stopping connector piece 80 in the mounted position on connector 70.

Vertical faces 711, 721, 731, and 741 therefore function as a first stopper for connector piece 80.

Conversely, when connector piece 80 is slid in the direction of arrow R for removal from connector 70, engaging members 811, 821 contact the backs of vertical faces 721 and 741 of engaging parts 72 and 74, thus stopping connector piece 80 in the original position on connector 70. The backs of vertical faces 721 and 741 thus function as second stoppers for connector piece 80.

Construction of Terminals and Electrodes

In connector 70, terminals 751–756 are respectively disposed inside holes 761, 762, 763, 764, 765, and 766 formed in connector 70. A cross section through where terminals 753 and 756, operating pin 838, and electrodes 833 and 836 are formed is shown in FIG. 16.

As shown in FIG. 16, connector piece 80 is constructed with cover member 806 covering outside case 805 in which circuit board 85 can be housed. Holes 863 and 866 are formed in cover member 806, and annular ridge members 843 and 846 are formed around the open lip at the bottom of the holes. Electrodes 833 and 836 are disposed inside holes 863 and 866. Electrode 833 is secured by screw 881, and electrode 836 is secured between circuit board 85 and cover member 806. A water-resistant packing 873 and 876 is also fit to electrodes 833 and 836. Electrodes 833 and 836 are electrically connected to the circuit pattern of circuit board 85 disposed inside connector piece 80.

This electrode structure is the same for the electrodes other than electrodes 833 and 836, i.e., electrodes 831, 832, 834, and 835. Note that the leads of cable 20 are also electrically connected to the circuit pattern on circuit board 85 by soldering.

Click Mechanism Configuration

Connector 70 is constructed with the recess therein covered by cover member 706. Holes 763 and 766 are formed in cover member 706. Inside these holes 763 and 766 terminals 753 and 756 are disposed as retractable pins of which the tips project from holes 763 and 766. A coil spring 773 and 776 is disposed to the flange 783 and 786 formed at the base end of each terminal 753 and 756, and terminals 753 and 756 are pushed in the direction protruding from holes 763 and 766 by coil springs 773 and 776. However, because the outside diameter of flanges 783 and 786 is greater than the inside diameter of holes 763 and 766, terminals 753 and 756 will not slip out from holes 763 and 766. This terminal structure is the same for the terminals other than terminals 753 and 756, i.e., terminals 751, 752, 754, and 755.

Because connector piece 80 is slid over connector 70 when connector piece 80 is mounted to connector 70, terminals 753 and 756 move over annular ridge members 843 and 846 of connector piece 80 while being pushed out by coil springs 773 and 776, and thus positively contact electrodes 833 and 836. Because a click-lock mechanism is thus achieved using annular ridge members 843 and 846, terminals 753 and 756, and coil springs 773 and 776 as thus described, connector piece 80 can be reliably connected to connector 70.

Note that to achieve a click configuration of this type it is also possible to provide terminals using retractable pins on the connector piece 80 side, and provide the annular ridge members on the connector 70, opposite the arrangement of the present embodiment.

Switch Mechanism Configuration

Hole 868 is formed in cover member 806 of connector piece 80, and operating pin 838 is disposed in this hole 868. This operating pin 838 is disposed to be retractable inside hole 868 with the tip thereof projecting from hole 868. A leaf spring type switch spring 88 is disposed to flange 898 formed on the base of operating pin 838. Switch spring 88 pushes operating pin 838 by means of the end 885 thereof in the direction projecting from hole 868. However, because the outside diameter of flange 898 is greater than the inside diameter of hole 868, operating pin 838 will not slip out from hole 868. Switch spring 88 is fastened with the base thereof held by screw 881 to the top of operating pin 838, and is thus electrically connected to electrode 833.

While not shown in the figure, note also that end 885 of switch spring 88 comprises a contact part contacting the base of operating pin 838, and a contact formed on the part extending to the side therefrom. This contact is electrically connected to the circuit pattern of circuit board 85, and this circuit pattern is inserted between first capacitor C1 and electrode 833.

Therefore, when connector piece 80 is not mounted on connector 70, operating pin 838 is pushed out by switch spring 88 with the end projecting from hole 868 as shown by the solid line in FIG. 16. Referring to FIG. 13, first switch SW1 therefore closes and first capacitor C1 becomes electrically connected in parallel to LED 31. As a result, even if a high potential charge caused by static electricity contacts electrodes 832 and 833, the charge is stored to first capacitor C1, and LED 31 is not damaged.

When connector piece 80 is mounted on connector 70, operating pin 838 moves in the direction into hole 868 as shown by the dot-dot-dash line in FIG. 16, and switch spring 88 is deformed as shown by the dot-dot-dash line. As a result, first switch SW1 in FIG. 13 is open, and a circuit configuration capable of measuring the pulse is completed. In addition, even if a charge is stored to first capacitor C1, the charge will not be discharged through electrodes 832 and 833 and terminals 752 and 753 to connector 70 and the circuits contained in main unit 10.

It should also be noted that a switching mechanism of this configuration is also formed for phototransistor 32. This switching mechanism is identical to that of LED 31, and further description thereof is therefore omitted below.

Operation

The operation of pulse wave information measuring apparatus 1 thus comprised is described briefly below with reference to FIGS. 1A, 1B, and 11.

Referring first to FIGS. 1A–B, when pulse wave information measuring apparatus 1 is used as a conventional wristwatch, cable 20 and sensor unit 30 are disconnected from connector 70 of main unit 10 and a separate connector cover is mounted on connector 70. This connector cover may be constructed identically to connector piece 80, except that no electrodes or similar electrical components are needed.

To measure the pulse rate while running using pulse wave information measuring apparatus 1, connector piece 80 is mounted on connector 70 to connect cable 20 to main unit 10, and main unit 10 is then secured to the arm using wrist band 12.

Sensor unit 30 is then secured tightly to the base of the finger by sensor securing band 40, and the user exercises or goes running. Because cable 20 can be shortened if sensor unit 30 is worn at the base of the index finger, cable 20 will not get in the way while running. Measuring the body temperature distribution from the palm to the fingertips has shown that the temperature drop at the base of the finger is relatively low compared with the sharp drop in temperature at the fingertips in cold weather. As a result, it is possible to reliably measure the pulse rate even when running outdoors on a cold day if sensor unit 30 is worn at the base of the finger.

When light is emitted toward the finger from LED 31 in this state as shown in FIG. 11, part of the light reaching the blood vessels is absorbed by hemoglobin in the blood, and part is reflected. The light reflected from the finger (blood vessels) is detected by phototransistor 32, and the change in detected light quantity corresponds to the change in blood volume (blood pulse wave). Specifically, when the blood volume is great, the reflected light is weak; when the blood volume decreases, the reflected light becomes stronger. As a result, the pulse rate and other blood information can be detected by monitoring the change in reflected light intensity.

To accomplish such measurements, the signal input from phototransistor 32 (sensor unit 30) is converted to a digital signal, and the pulse count is calculated by data processing circuit 50 shown in FIG. 12 performing a frequency analysis or other suitable operation on this digital signal. The pulse count obtained from this calculation is then displayed on LCD 13.

Referring again to FIG. 11, part of the light emitted from LED 31 travels through the finger and reaches the blood vessels as shown by arrow C, and the light reflected from hemoglobin in the blood travels back to phototransistor 32 as shown by arrow D. Part of the light emitted from LED 31 is also reflected at the finger surface as shown by arrow E, and travels back to phototransistor 32. Part of the light emitted from LED 31, and part of the light reflected from the blood vessels, is absorbed or diffused inside the finger as shown by arrows F and G, and does not reach phototransistor 32.

Sensor unit 30 uses an LED 31 with a 350 nm to 600 nm emissions wavelength range, and phototransistor 32 with a 300 nm to 600 nm detection wavelength range, and the biological data is expressed based on the detection results in the overlapping wavelength range from approximately 300 nm to approximately 600 nm. External light with a wavelength of 700 nm or less tends to not pass easily through the finger. Thus, even if the finger area not covered by sensor unit holding band 40 is exposed to external light, this light does not reach phototransistor or photodetector 32 by traveling through the finger as an optical conductor.

The reasons for this are described below with reference to FIG. 17A and FIG. 17B. FIG. 17A is a graph of the relationship between optical wavelength and the optical transmittance of the skin. In this figure, dotted line α indicates the transmittance characteristic with 200 nm wavelength light; dotted line b, the transmittance characteristic with 300 nm wavelength light; dotted line c, the transmittance characteristic with 500 nm wavelength light; dotted line d, the transmittance characteristic with 700 nm wavelength light; and dotted line e, the transmittance characteristic with 1 μm wavelength light.

As will be obvious from this figure, because external light in the wavelength range below 700 nm does not pass easily through the skin, external light incident to any part of the finger not covered by sensor unit holding band 40 will not pass through the finger to phototransistor 32, as shown by dotted line X in FIG. 11. On the other hand, if an LED with an emissions peak near 880 nm and a silicon phototransistor are used, the detection wavelength will range from 350 nm to 1200 nm. Because light with a 1 μm wavelength (dotted line e in FIG. 17A) passes easily through the skin and can therefore reach the photodetector using the finger as an optical conductor as shown by arrow Y in FIG. 11, detection errors caused by variations in the external light can easily occur using a detection wavelength ranging from 350 nm to 1200 nm.

It should be noted that if the objective is to obtain pulse information without the influence of external light, a GaP type LED having a primary emissions range from 540 nm to 570 nm as shown in FIG. 18, and a GaP type phototransistor with a sensitivity range from 200 nm to nearly 700 nm as shown in FIG. 19, may also be used.

Moreover, the signal-to-noise (S/N) ratio of the pulse signal based on the blood volume change is high because the pulse wave information is obtained using light in the wavelength range from approximately 300 nm to approximately 700 nm. Specifically, the absorption characteristic of hemoglobin not bonded with oxygen is shown by curve Hb in FIG. 17B, and the absorption characteristic of hemoglobin bonded with oxygen is shown by curve HbO$_2$. As these curves show, the absorption coefficient of hemoglobin in the blood to light of a wavelength from 300 nm to 700 nm is great, and is several times to approximately 100 times the absorption coefficient with conventionally detected light, 880 nm wavelength light. The detection rate (S/N ratio) of the pulse based on the blood volume change is therefore high because the detection value varies sensitively to the blood volume change if light in the wavelength range for which the absorption coefficient is high (300 nm–700 nm) is used as the detected light based on the absorption characteristics of hemoglobin.

Major Effects of the Embodiment

As described above, pulse wave information measuring apparatus 1 according to the present embodiment provides convenient portability, thus enabling the pulse count and other pulse information to be measured while running.

Unlike the conventional method whereby the belt tightness must be adjusted with the surface fastener each time the sensor unit is put on, sensor unit 30 can be pressed against the finger with appropriate force by simply fitting the sensor unit holding band 40 to the finger if the sensor unit holding band has been sized appropriately to the finger because sensor unit 30 is held on the finger by means of sleeve-like sensor unit holding band 40 with pulse wave information measuring apparatus 1. The pulse signal detection sensitivity is therefore also consistently high.

The finger surface can also be uniformly held tight to the entire outside surface of the light transmittance plate because outside surface 341 of light transmittance plate 34 is positioned projecting outside of the reference surface (outside surface 361 of sensor frame 36) in sensor unit 30 as shown in FIG. 20A-1. Even if the position of the finger shifts slightly, as seen from FIG. 20A-2, the finger remains in contact with the entire outside surface 341 of light transmittance plate 34.

Referring to FIG. 20B-1 and FIG. 20B-2, if outside surface 31D of light transmittance plate 34D is recessed, however, and the position of the finger to the light transmittance plate 34D is shifted, the finger will not cover the corners of light transmittance plate 34D. This introduces a layer of air in the corner areas not covered by the finger, and prevents detection of the pulse signal. An air layer also covers a large part of the space between light transmittance plate 34D and the finger even if the position of the finger is shifted only slightly as shown in FIG. 20B-2. As a result, sensitivity drops significantly when the finger moves while running, for example, if the outside surface of light transmittance plate is recessed.

Residual blood in the blood vessels pressurized by the light transmittance plate is also purged to the sides from that area as shown by the white circles in FIGS. 21A and 21B when the outside surface 341 of light transmittance plate 34 is pressed against the skin with sensor unit 30 according to the present embodiment. As a result, the signal detected by phototransistor 32 is minimally affected by residual blood in the blood vessels. More specifically, the signal detected by phototransistor 32 contains signal components from residual blood and signal components from flowing blood, and the pulse count is determined from the flowing blood signal component. The signal component from residual blood is therefore background noise to the desired detection signal, and sensitivity can therefore be improved by taking measurements after purging any residual blood.

The effectiveness of this method can be confirmed from the study results shown in FIGS. 22–27.

The relationship between the load (pressure) on the finger surface, the level of the AC signal component (solid lines P1, P3) contained in the detected signal, and the level of the DC signal component (solid lines P2, P4), was evaluated using a sensor unit according to the prior art in which the outside surface 341D of light transmittance plate 34D is recessed from the reference surface 0.2 mm as shown in FIG. 20B. The results from two of many repeated evaluations are shown in FIGS. 22 and 23.

The AC signal component (AC) in these evaluations is the signal component based on the flow of blood through the blood vessels, and corresponds to the pulse signal. The DC signal component (DC) is the signal based on noise and other factors. As shown by these figures, sensitivity increases as the AC signal component in the detected signal increases.

Based on the results shown in FIG. 22, the AC:DC signal component ratio was obtained, and the relationship between this ratio and the pressure of the sensor unit on the finger surface is shown in FIG. 24.

With the sensor units used in this comparison, the AC component level is low at approximately 6 mV even when a high load is applied as shown in FIG. 22 and FIG. 23. In addition, the AC:DC component ratio is not high unless a load exceeding approximately 110 gf is applied as shown in FIG. 24.

The relationship between the load (pressure) on the finger surface, the level of the AC signal component (solid lines P5, P7) contained in the detected signal, and the level of the DC signal component (solid lines P6, P8), was also evaluated using a sensor unit 30 according to the preferred embodiment in which the outside surface 341 of light transmittance plate 34 projects 0.25 mm from the reference surface as shown in FIGS. 20A-1 and 20A-2. The results from two of many repeated evaluations using sensor unit 30 are shown in FIGS. 25 and 26. Based on the results shown in FIG. 25, the AC:DC signal component ratio was obtained, and the relationship between this ratio and the pressure of sensor unit 30 on the finger surface is shown in FIG. 27.

Using the sensor unit 30 of the preferred embodiment, the AC component level exceeds 7 mV and is stable even when a relatively small load is applied as shown in FIGS. 25 and 26. As shown in FIGS. 25 and 27, the AC:DC component ratio is high and stable when a load ranging anywhere from 30 gf to 230 gf is applied. Sensitivity was thus confirmed to be high.

Unlike the conventional sensor unit, little pressure is required to achieve consistently high sensitivity with sensor unit 30 according to the present embodiment, and there is therefore no discomfort when wearing sensor unit 30.

The surface of the finger also reliably contacts body ground terminal 38 with sensor unit 30 according to the present invention because outside surfaces 381 of body ground terminals 38 project outside the reference surface (outside surface 361 of sensor frame 36) as shown in FIGS. 20A-1 and 20A-2. Because outside surfaces 381 of body ground terminals 38 are below outside surface 341 of light transmittance plate 34, outside surfaces 381 of body ground terminals 38 do not prevent achieving tight contact between the finger surface and outside surface 341 of light transmittance plate 34.

Furthermore, because body ground terminals 38 are positioned on opposite sides of light transmittance plate 34, positive contact between the finger and at least one body ground terminal 38 is maintained even when the finger shifts slightly off light transmittance plate 34.

Alternative Embodiment of the Sensor Unit

It should be noted that while outside surface 341 of light transmittance plate 34 is flat in the present embodiment, outside surface 341A of light transmittance plate 34A may also be convex as shown in FIG. 28. Contact between the finger and outside surface 341A of light transmittance plate 34A can therefore be improved because sufficient pressure against light transmittance plate 34A is achieved by placing the finger lightly against outside surface 341A of light transmittance plate 34A.

In addition, while sensor unit 30 (pulse signal detector) is provided on the end of cable 20 in this embodiment because pulse wave information measuring apparatus 1 is worn on the wrist, the same effects can be achieved when the pulse signal detector is integrated into the surface of main unit 10 if a structure in which the outside surface of light transmittance plate 34A projects outward is used. A pulse wave information measuring apparatus thus comprised is not limited to use on the finger, and can be used to measure pulse information at the wrist, ear lobes, and other skin surface areas while achieving the same effects as the present embodiment.

Embodiment 2

A second embodiment of a pulse wave information measuring apparatus according to the present invention is described next below. The basic construction of this pulse wave information measuring apparatus is identical to that of the first embodiment above. Like parts in the first and second embodiments are therefore identified with like references, and further detailed description thereof is omitted below.

Sensor Unit Configuration

FIGS. 29-31 are used below to describe the sensor unit used in the pulse wave information measuring apparatus of the present embodiment, and correspond to FIGS. 5-7 referenced in the first embodiment above. Specifically, FIG. 29 is a cross-sectional view taken along line I—I' in FIG. 4; FIG. 30 is a cross-sectional view taken along line II—II' in FIG. 4; and FIG. 31 is a cross-sectional view taken along line III—III' in FIG. 4.

As will be known from these figures, the basic construction of sensor unit 30 used in the pulse wave information measuring apparatus of the present embodiment is identical to that of the first embodiment above, and is worn at the base of the index finger (body) by means of a sleeve-like sensor unit holding band 40 made from a stretch material.

A projection 303 (sensor unit slipping prevention means) used to prevent the position of sensor unit 30 from slipping inside sensor unit holding band 40 is provided on the back of back cover 302 of sensor unit 30. The tip of projection 303 is pointed in this embodiment. When sensor unit 30 is then worn between the finger and sensor unit holding band 40, projection 303 bites lightly into sensor unit holding band 40, and sensor unit 30 is thereby prevented from slipping.

Projection 303 is also formed directly opposite light transmittance plate 34 of sensor unit 30. As a result, the force of sensor unit holding band 40 pressing sensor unit 30 against the finger is concentrated on light transmittance plate 34 when sensor unit 30 is held on the finger by sensor unit holding band 40.

As in the first embodiment above, outside surface 341 of light transmittance plate 34 projects above the reference surface, which as used herein means the outside surface 361 of sensor frame 36 surrounding light transmittance plate 34. As shown in FIG. 30, two body ground terminals 38 are fixed in sensor frame 36 by screws 306 on opposing sides of light transmittance plate 34. These body ground terminals 38 contact the finger surface when light transmittance plate 34 is worn against the finger. Body ground terminals 38 also project above the reference surface (outside surface 361 of sensor frame 36). However, outside surfaces 381 of body ground terminals 38 (i.e., the finger contact surfaces) are positioned lower than outside surface 341 of light transmittance plate 34, i.e., are positioned at a height between the reference surface and the outside surface 341 of light transmittance plate 34.

Sensor Unit Holding Band

FIG. 32A is a perspective view of the sensor unit holding band 40 holding sensor unit 30 on the finger as shown in FIG. 11, and FIG. 32B is a perspective view of the sensor unit holding band turned upside down.

FIG. 33A is a perspective view of the sensor unit holding band 40 inverted from the condition shown in FIG. 32A, and FIG. 33B is a perspective view of the sensor unit holding band inverted from the condition shown in FIG. 32B.

The shape of sensor unit holding band 40 in these figures suggests a sleevelike shape with fingerholds 421 and 413 formed lengthwise from one end of sensor unit holding band 40. These fingerholds 421 and 413 are used to pull sensor unit holding band 40 on to the base of the finger.

As shown in FIG. 32A and FIG. 32B, a sensor unit slipping prevention means 43 (sensor unit slipping prevention means) is formed on the inside circumferential surface of sensor unit holding band 40 by sewing the two ends of rubber belt 430 (elastic body) oriented circumferentially to sensor unit holding band 40 at the palmside of the finger. Cable 20 is then held securely near the connection to sensor unit 30 by rubber belt 430 by stretching rubber belt 430, passing sensor unit 30 under and releasing rubber belt 430, and then pulling the rest of cable 20 back out from sensor unit holding band 40. When sensor unit holding band 40 thus comprised is then worn on the finger, light transmittance plate 34 of sensor unit 30 can be held securely against the finger as shown in FIG. 11. Sensor unit holding band 40 also prevents sensor unit 30 inside thereof from slipping, and prevents sensor unit 30 from slipping out from sensor unit holding band 40, during pulse wave measurements.

Note that sensor unit holding band 40 must be able to shield light transmittance plate 34 from external light, and exert sufficient pressure to hold sensor unit 30 firmly against the surface of the finger. In the present embodiment, therefore, sensor unit holding band 40 is sewn together from strips of a fabric such as that used on diving wet suits. The components used to manufacture sensor unit holding band 40 are shown in FIGS. 34A to 34D. More specifically, sensor unit holding band 40 is manufactured from a first sheet 41 forming the bulk of the holding band, second sheet 42 forming the bottom of the holding band, and filler tapes 44 and 45. Filler tapes 44 and 45 are applied inside sensor unit holding band 40 to cover the seams between first sheet 41 and second sheet 42.

Of these two sheet pieces, sensor unit slipping prevention means 43 formed by sewing the ends of rubber belt 430 is attached to first sheet 41. One end of first sheet 41 is cut with two flats 411 and 412, and curved concave parts 417 and 418 forming a projection therebetween that becomes fingerhold 413. A similar projection that becomes fingerhold 421 is also formed on second sheet 42.

To form sensor unit holding band 40, first sheet 41 and second sheet 42 are sewn together with edges 415 and 425, and edges 416 and 426, butted together as shown in FIGS. 35A-35D. Because there are therefore no overlapping seams, it is more difficult for gaps to form when sensor unit holding band 40 is worn on the finger.

Filler tapes 44 and 45 are then applied over the seams so that the seams (joints) are not exposed on the inside surface of sensor unit holding band 40. By thus finishing the seams to be flat, there is no discomfort when sensor unit holding band 40 is fit onto the finger, and there are no gaps between the finger and sensor unit holding band 40.

A thick material such as that used for diving wet suits is used for sensor unit holding band 40 in the present embodiment. This material is a compound material comprising a synthetic jersey or other stretch fabric applied to both front and back of the foamed rubber core layer (e.g., a polyurethane rubber layer). This imparts an appropriate elasticity to the sensor unit holding band 40, particularly in the circumferential direction. Therefore, when sensor unit 30 is fixed to the finger surface using this sensor unit holding band 40, pulse signal detection sensitivity is stable because sensor unit holding band 40 exerts a consistent pressure controlled by the size of sensor unit holding band 40 and the circumference of the finger (ring size). While described in greater detail below, pulse signal detection sensitivity is high when the pressure holding sensor unit 30 against the finger is in an appropriate range, and tends to drop when the pressure is above or below this appropriate range. With the sensor unit holding band 40 of the present embodiment, however, a constant appropriate pressure is applied by simply wearing the sensor unit holding band 40 on the finger, and detection sensitivity is therefore consistently high.

Sensor unit holding band 40 is stretched in the circumferential direction when it is fit onto the finger, but external light is still unable to pass through sensor unit holding band 40 in this stretched condition because it comprises a middle layer of foam rubber. When sensor unit holding band 40 is manufactured from material such as that used in swimming suits, there are no problems with elasticity or opacity in the unstretched state, but these materials provide insufficient opacity when stretched. In addition, when a swimming suit material or similar material is used and sensor unit holding band 40 gets wet while getting a drink during a marathon, for example, the material stretches and sags, and does not return completely to the original dimensions after it dries. While these dimensional problems present no real problem in large articles such as a swimming suit, they do present a significant problem on small articles such as sensor unit holding band 40, particularly when it is necessary to avoid creating gaps. These problems do not arise, however, when sensor unit holding band 40 is manufactured from a compound material such as that described in the present embodiment.

The material used for sensor unit holding band 40 according to the present embodiment also offers a comfortable texture and does not fray when the components are cut out because it is a compound fabric comprising a synthetic fabric applied over a foam rubber layer. It is therefore possible to sew the cut parts together without basting or hemming the edges to prevent fraying. Less time is therefore required to manufacture sensor unit holding band 40, and there is no unnecessary unevenness on the inside circumferential surface of sensor unit holding band 40 as shown in FIG. 35A and FIG. 35D. In addition, hemming the cut edges to prevent fraying contributes to instability in the diameter of sensor unit holding band 40. This dimensional inconsistency leads in turn to variations in the force holding sensor unit 30 against the finger, and adversely affects the pulse signal detection sensitivity.

Sensor unit holding band 40 according to the present embodiment, however, is finished substantially to the pattern dimensions to which the sheet pieces are cut. Dimensional stability is therefore high, there is little variation in the force holding sensor unit 30 against the finger, and the pulse signal detection sensitivity is therefore stable.

Because a compound fabric comprising a synthetic fabric applied to a layer of foam rubber is used for sensor unit holding band 40, a cylindrical shape such as that shown in FIG. 32A and FIG. 32B is retained even when sensor unit holding band 40 is taken off the finger. It is therefore possible to insert the finger to sensor unit holding band 40 by simply pulling up on the fingerholds. The fabric used for sensor unit holding band 40 is also strong, and exhibits sufficient durability when used, for example, to measure the pulse while exercising.

It should also be noted that fabrics of different colors may be used for the front and back sides of the foam rubber layer, and these different colors make it simple to identify the inside and outside of sensor unit holding band 40. Moreover, when sensor unit holding band 40 is manufactured to different sizes, the color of the outside-facing fabric can be varied by size to enable quick, simple identification of different sizes.

Relationship Between Pulse Signal Detection Sensitivity and Sensor Unit Pressure on the Finger Surface If sensor unit holding band 40 according to the present embodiment is provided, for example, in three sizes, appropriate pressure between sensor unit 30 and the finger can be consistently maintained, and the pulse signal detection sensitivity consistently high, even when pulse wave information measuring apparatus 1 according to the invention is used by persons with fingers of different sizes.

The relationship between the circumferential size of the finger ("ring size" below) and the load applied from sensor unit 30 to the finger surface when sensor unit holding band 40 according to the present embodiment is worn on the finger is shown in FIG. 36. Shown in FIG. 36 is the relationship between the ring size and the load applied from sensor unit 30 to the finger surface when sensor unit holding bands 40 of the selected sizes shown in Table 1 are used. Note that the dimensions shown in Table 1 (dimensions A, B, L, D, and E) correspond to the same dimensions shown in FIG. 34A, FIG. 34B, and FIGS. 35A–35D.

TABLE 1

| Size | dim. A | dim. B | dim. L | dim. D | dim. E |
|------|--------|--------|--------|--------|--------|
| S | 42 mm | 49 mm | 39 mm | 50 mm | 60 mm |
| M | 46 mm | 53 mm | 41 mm | 54 mm | 64 mm |
| L | 49 mm | 56 mm | 43 mm | 57 mm | 69 mm |

As shown in FIG. 36, determining the sizes of sensor unit holding band 40 results in a linear relationship between the ring size and the load applied from sensor unit 30 to the finger surface. In other words, based on the sleeve-like sensor holding method of the present invention, the load applied from sensor unit 30 to the finger surface is substantially constant insofar as the user determines the size of sensor unit holding band 40 appropriate to the user's finger and uses the selected sensor unit holding band 40 to hold sensor unit 30 on the finger. Moreover, the load applied from sensor unit 30 to the finger surface with the method of the present invention is more consistent than other conventional methods, including methods using a belt and buckle design whereby plural holes are provided lengthwise to a belt-like strap holding the sensor unit, and the belt is held by hooking the appropriate hole on a pin, and surface fastener methods whereby a Velcro®)like material is used to adjust the tightness as described above.

The relationship between the load applied from sensor unit 30 to the finger surface and the pulse signal detection sensitivity was investigated using sensor unit 30 with a total surface area of approximately 144 mm² and a light transmittance plate 34 area of approximately 40 mm² as shown in FIG. 37 with light transmittance plate 34 projecting above the surrounding area as shown in FIGS. 29–31. The results of this evaluation are shown in FIG. 38 and FIG. 39. Note that the finger is pressed hard against light transmittance plate 34, and lightly against the surrounding area.

The data shown in FIG. 38 and FIG. 39 was obtained from measurements obtained by pressing sensor unit 30 against the finger surface using two subjects with different ring sizes. The AC signal component (AC) in these figures is the signal component based on blood flow through the blood vessels, and corresponds to the pulse signal. The DC signal component (DC) is the signal based on noise and other factors. As shown by these figures, sensitivity increases as the AC signal component in the detected signal increases.

As shown in FIG. 38 and FIG. 39, the pulse signal detection sensitivity is high when the pressure holding sensor unit 30 against the finger surface is within an appropriate range, and tends to drop when the pressure is above or below this appropriate range. For example, based on the measurement results shown in FIG. 38, the AC component level is stable at a relatively high level when the load per unit area of light transmittance plate 34 is in the range from approximately 40 gf/40 mm² to approximately 180 gf/40 mm². Based on the measurement results shown in FIG. 39, the AC component level is stable at a relatively high level when the load per unit area of light transmittance plate 34 is in the range from approximately 40 gf/40 mm² to approximately 110 gf/40 mm². The pulse signal detection sensitivity is therefore stable at a relatively high level when the load per unit area of light transmittance plate 34 with sensor unit 30 pressed against the finger is in the range from approximately 40 gf/40 mm² to approximately 110 gf/40 mm². In simplified terms, the pulse signal detection sensitivity is stable at a relatively high level when the load per unit area of light transmittance plate 34 with sensor unit 30 pressed against the finger is in the range from approximately 1.0 gf/mm² to approximately 2.8 gf/mm².

Relationship Between Pulse Signal Detection Sensitivity and the Depression Depth of the Sensor Unit into the Finger The relationship between pulse signal detection sensitivity and the depth of sensor unit 30 depression into the finger was investigated while taking the measurements of which the results are shown in FIG. 38. The results are shown in FIG. 40. The relationship between the AC and DC component levels detected by sensor unit 30 in the study shown in FIG. 38, and the displacement of sensor unit 30 when sensor unit 30 is pressed into the finger from a position resting on the finger surface, is plotted in FIG. 40. This relationship was also investigated while taking the measurements of which the results are shown in FIG. 39, and the results are shown in FIG. 41. Note that the pulse signal detection sensitivity can also be concluded to increase as the AC component level increases.

As will be known from FIG. 40 and FIG. 41, the pulse signal detection sensitivity is high when the displacement of sensor unit 30 (depression depth into the finger) is in an appropriate range because the force pressing sensor unit 30 into the finger is in the appropriate range. However, the pulse signal detection sensitivity tends to drop when the displacement of sensor unit 30 (depression depth into the finger) is above or below this appropriate range. For example, based on the measurement results shown in FIG. 40, the AC component level is stable at a relatively high level when the displacement is in the range from approximately 2.0 mm to approximately 4.0 mm. Based on the measurement results shown in FIG. 41, the AC component level is stable at a relatively high level when the displacement is in the range from approximately 2.0 mm to approximately 3.0 mm. The pulse signal detection sensitivity is therefore stable at a relatively high level when the displacement from pressing sensor unit 30 into the finger is in the range from approximately 2.0 mm to approximately 3.0 mm.

After multiple repetitions of the investigation described above, it was determined that the pulse signal detection sensitivity is stable at a relatively high level when the displacement from pressing sensor unit 30 into the finger is in the range from approximately 2.2 mm to approximately 2.7 mm.

More specifically, the pulse signal detection sensitivity is stable at a relatively high level when the load per unit area of light transmittance plate 34 with sensor unit 30 pressed against the finger is in the range from approximately 40 gf/40 mm² to approximately 100 gf/40 mm². In simplified terms, the pulse signal detection sensitivity is stable at a relatively high level when the load per unit area of light transmittance plate 34 with sensor unit 30 pressed against the finger is in the range from approximately 1.0 gf/mm² to approximately 2.5 gf/mm².

Therefore, if sensor unit holding band 40 according to the present embodiment is provided, for example, in the three sizes shown in FIG. 36 and Table 1, sensor unit 30 can be worn on the finger in an appropriate condition by users whose ring size is between 55 mm to 70 mm insofar as the appropriately sized sensor unit holding band 40 is selected and used. More specifically, except for unusual cases, the ring size at the base of the index finger is greater than approximately 55 mm even in people with the most slender fingers, and is less than approximately 70 mm even in people with the thickest fingers. All users can therefore select an appropriately sized sensor unit holding band 40 whereby the load is within the shaded area in FIG. 36, and thereby assure that the load on sensor unit 30 per unit area of light transmittance plate 34 is within the range of approximately 40 gf/40 mm² to approximately 100 gf/40 mm² (in simplified terms, the load per unit area of light transmittance plate 34 with sensor unit 30 pressed against the finger is in the range from approximately 1.0 gf/mm² to approximately 2.5 gf/mm²). Expressed in terms of the displacement when sensor unit 30 is pressed into the finger, a depression depth of approximately 2.2 mm to approximately 2.7 mm can be achieved.

As described with reference to FIG. 21 in the first embodiment above, the reason why this relationship between the pulse signal detection sensitivity and the pressure and depression depth of sensor unit 30 is exhibited is because residual blood in the blood vessels (the white dots in FIG. 21) is purged to the sides when the pressure and depression depth are appropriate. As a result, the effects of residual blood on the detection results are reduced compared with when there is little or no pressure applied. More specifically, the signal detected by phototransistor 32 contains signal components from residual blood and signal components from flowing blood, and the pulse count is determined from the flowing blood signal component. The signal component from residual blood is therefore background noise to the desired detection signal, and sensitivity can therefore be improved by taking measurements after purging any residual blood. It should also be noted that the sensitivity drop when the applied pressure is excessive is due to obstruction of the blood flow itself.

Operation

The operation of pulse wave information measuring apparatus 1 when sensor unit 30 is held on the finger by sensor unit holding band 40 according to the present embodiment is described briefly below.

Sensor unit 30 is passed under the stretched rubber belt 430 inside sensor unit holding band 40, and is then held in place with the base of cable 20 held by rubber belt 430.

Because fingerholds 413 and 421 are formed on the end of sensor unit holding band 40, these fingerholds 413 and 421 are then held to pull sensor unit holding band 40 up to the base of the finger.

Because cable 20 can be shortened if sensor unit 30 is worn at the base of the finger, cable 20 will not get in the way while running.

Measuring the body temperature distribution from the palm to the fingertips has shown that the temperature drop at the base of the finger is relatively low compared with the sharp drop in temperature at the fingertips in cold weather. As a result, it is possible to reliably measure the pulse rate even when running outdoors on a cold day if sensor unit 30 is worn at the base of the finger.

The pulse signal detection sensitivity will also be high and stable even while exercising insofar as sensor unit holding band 40 is sized appropriately to the user's finger according to the chart shown in FIG. 36, thereby assuring that the load on sensor unit 30 per unit area of light transmittance plate 34 is within the range of approximately 40 gf/40 mm$^2$ to approximately 100 gf/40 mm$^2$, and the depression depth of the displacement of sensor unit 30 pressed into the finger is in the range from approximately 2.2 mm to approximately 2.7 mm.

Major Effects of the Embodiment

As described hereinabove, sensor unit holding band 40 according to the present embodiment used in pulse wave information measuring apparatus 1 is a sleeve-like band. Therefore, unlike conventional surface fastener and other adjustable fastening methods, sensor unit 30 can be pressed with appropriate force against the finger by simply putting sensor unit holding band 40 on the finger insofar as the size of sensor unit holding band 40 is selected appropriately to the ring size of the user's finger on which sensor unit holding band 40 is worn. Specifically, the load applied from sensor unit 30 to the finger surface can be controlled to within the optimum load range of approximately 1.0 gf/mm$^2$ to approximately 2.8 gf/mm$^2$ (2.5 gf/mm$^2$) per unit area of light transmittance plate 34. The pulse signal detection sensitivity is therefore also high as a result. It is also not necessary to adjust the tension in order to achieve high pulse signal detection sensitivity when sensor unit 30 is fastened to the finger.

Furthermore, external light will not pass through sensor unit holding band 40 even when it is stretched on the finger because a thick material such as that used for diving wet suits and having a middle layer of foam rubber is used for sensor unit holding band 40. The dimensional stability of sensor unit holding band 40 is also good when the band is wet, and gaps therefore do not occur. The pulse signal can therefore be detected in a stable condition without being affected by external light.

The material does not fray at the edges when cut into the component parts because the material used for sensor unit holding band 40 according to the present embodiment is a compound fabric comprising a synthetic fabric applied over a foam rubber layer. It is therefore not necessary to baste or hem the edges to prevent fraying. Moreover, surface roughness that can permit penetration of external light, and size variations in sensor unit holding band 40 that can lead to inconsistent detection sensitivity, do not occur because there are no unnecessary folded seams.

Sensor unit slipping prevention means 43 is also formed from projection 303 provided on the back of sensor unit 30, and rubber belt 430 disposed on the inside circumferential surface of sensor unit holding band 40 on the palm-side of the finger. As a result, sensor unit 30 is prevented from shifting inside sensor unit holding band 40 and from falling out of sensor unit holding band 40.

The force of sensor unit holding band 40 pressing sensor unit 30 against the finger is also concentrated on light transmittance plate 34 when sensor unit 30 is held on the finger by sensor unit holding band 40 because projection 303 formed on the back of sensor unit 30 is directly opposite light transmittance plate 34. The pulse signal can therefore be detected with high sensitivity because positive contact between light transmittance plate 34 and the finger is assured. It is also easy to design sensor unit holding band 40 and sensor unit 30 to achieve an optimum load applied from sensor unit 30 to the body surface because it is easy to control the load applied from sensor unit 30 to the finger surface.

It is also simple to regulate the load on sensor unit 30 and the displacement of pressure applied to sensor unit 30 because the contact area between the finger surface and sensor unit 30 can be easily determined if outside surface 341 of light transmittance plate 34 extends outside of the reference surface (outside surface 361 of sensor frame 36).

Other Embodiments

While the main unit and sensor unit are described in the preceding embodiments as being connected by a cable, it will be obvious that signals can also be communicated by means of wireless transmissions.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

REFERENCE NUMERALS 1 pulse wave information measuring apparatus (pulse wave information measuring apparatus)
10 main unit
12 wrist band
13 liquid crystal display device (display)
20 cable
30 sensor unit (pulse signal detector)
31 LED
32 phototransistor
34 light transmittance plate
36 sensor frame
38 body ground terminal
40 sensor unit holding band
41 first sheet
42 second sheet
43 sensor unit slipping prevention means
50 data processing circuit
70 connector
80 connector piece
300 component housing 341 outside surface of the light transmittance plate (finger contact surface)
361 outside surface of the sensor frame (reference surface)
381 outside surface of the body ground terminal (finger contact surface)
303 sensor unit projection (sensor unit slipping prevention means)
430 rubber belt

What is claimed is:

1. A pulse wave measuring apparatus comprising
   a sensor unit comprising:
   a light emitting element for emitting light to a surface of a body, and
   a receptor element for detecting the light emitted from said light emitting element and reflected back from the body;
   a light transmittance plate disposed on a first side of said receptor element and a first side of said light emitting element facing the body, wherein an outside surface of said light transmittance plate faces the body, wherein the outside surface of the light transmittance plate is exposed above a reference surface, and wherein the reference surface is an outside surface of said sensor unit surrounding said light transmittance plate;
   a main unit comprising a data processor for obtaining pulse information in accordance with a pulse signal detection signal supplied from said sensor unit; and
   a sleeve-like sensor unit holding band, wherein said holding band is elastic in at least a circumferential direction, wherein said sensor unit holding band cooperates with the exposed outside surface of said light transmittance plate so as to secure said sensor unit against the surface of the body, wherein said light transmittance plate is arranged tightly against the surface of the body.

2. A pulse wave measuring apparatus according to claim 1, wherein the outside surface of said light transmittance plate is flat in shape.

3. A pulse wave measuring apparatus according to claim 1, wherein the outside surface of said light transmittance plate is convex in shape.

4. A pulse wave measuring apparatus according to claim 1, wherein said sensor unit holding band comprises a fabric having a foam rubber layer.

5. A pulse wave measuring apparatus according to claim 1, wherein said sensor unit holding band comprises a fabric having a polyurethane rubber layer.

6. A pulse wave measuring apparatus according to claim 1, wherein said sensor unit holding band comprises a fabric with elasticity on at least one of an inside and an outside circumferential surface of said holding band.

7. A pulse wave measuring apparatus according to claim 1, wherein said sensor unit holding band comprises a plurality of fabric pieces with edges thereof joined in a seam.

8. A pulse wave measuring apparatus according to claim 7, wherein a tape is disposed on an inside circumferential side of said sensor unit holding band covering having the seam arranged between adjacent ones of said plurality of fabric pieces of said sensor unit holding band.

9. A pulse wave measuring apparatus according to claim 1, wherein at least one of said sensor unit holding band and said sensor unit comprises a sensor unit slipping prevention means for preventing a shift in a position of said sensor unit inside said sensor unit holding band.

10. A pulse wave measuring apparatus according to claim 9, wherein said sensor unit slipping prevention means comprises a protrusion provided on said sensor unit projecting in a direction opposite to said light transmittance plate, and protruding into the inside circumferential surface of said sensor unit holding band.

11. A pulse wave measuring apparatus according to claim 1, wherein said sensor unit holding band further comprises a fingerhold extending in the lengthwise direction from the end of said band.

12. A pulse wave measuring apparatus according to claim 1 wherein said sensor unit holding band and sensor unit are comprised so that a load applied from said sensor unit to the body surface ranges from 1.0 gf/mm$^2$ to 2.8 gf/mm$^2$ per unit area of said light transmittance plate when said sensor unit is held to the surface of the body.

13. A pulse wave measuring apparatus according to claim 12, wherein said sensor unit holding band comprises a material having a foam rubber layer.

14. A pulse wave measuring apparatus according to claim 12, wherein the sensor unit holding band comprises a material having a polyurethane layer.

15. A pulse wave measuring apparatus according to claim 1, further comprising on a side of said sensor unit opposite said light transmittance plate a projection for focusing a force of said sensor unit holding band pressing said sensor unit against the surface of the body on said light transmittance plate.

16. A pulse wave measuring apparatus according to claim 1, further comprising a wrist band for wearing the main unit on a wrist, and
    a cable extending from said main unit to said sensor unit disposed on an end of said cable.

17. A pulse wave measuring apparatus comprising:
    a sensor unit comprising:
    a light emitting element for emitting light to a surface of a body, and
    a receptor element for detecting the light emitted from said light emitting element and reflected back from the body;
    a light transmittance plate disposed on a first side of said receptor element and a first side of said light emitting element facing the body, wherein an outside surface of said light transmittance plate faces the body, wherein the outside surface of the light transmittance plate is exposed above a reference surface, and wherein the reference surface is an outside surface of said sensor unit surrounding said light transmittance plate;
    a main unit comprising a data processor for obtaining pulse information in accordance with a pulse signal detection signal supplied from said sensor unit;
    a sleeve-like sensor unit holding band, wherein said holding band is elastic in at least a circumferential direction, so as to secure said sensor unit against the surface of the body, wherein said light transmittance plate is arranged tightly against the surface of the body; and
    a body ground terminal disposed on the outside surface of said sensor unit surrounding said light transmittance plate, and contacting the surface of the body when said light transmittance plate is disposed tightly against the surface of the body, and
    wherein an outside surface of said body ground terminal projects from the reference surface to a position lower than the outside surface of said light transmittance plate.

18. A pulse wave measuring apparatus comprising:
    a sensor unit comprising:

a light emitting element for emitting light to a surface of a body, and a receptor element for detecting the light emitted from said light emitting element and reflected back from the body;

a light transmittance plate disposed on a first side of said receptor element and a first side of said light emitting element facing the body, wherein an outside surface of said light transmittance plate faces the body;

a main unit comprising a data processor for obtaining pulse information in accordance with a pulse signal detection signal supplied from said sensor unit;

a sleeve-like sensor unit holding band, wherein said holding band is elastic in at least a circumferential direction, so as to secure said sensor unit against the surface of the body, wherein said light transmittance plate is arranged tightly against the surface of the body; and a cable connecting said main unit to said sensor unit at a cable connection area; and wherein at least one of said sensor unit holding band and said sensor unit comprises a sensor unit slipping prevention means for preventing a shift in a position of said sensor unit inside said sensor unit holding band, said sensor unit slipping prevention means comprising an elastic body having two ends fastened to an inside circumferential surface of said sensor unit holding band in a manner whereby said sensor unit position is fixed by passing said cable between said elastic body and the inside circumferential surface of said sensor unit holding band so that said cable is secured by said elastic body near the cable connection area.

19. A pulse wave measuring apparatus comprising:

a sensor unit comprising:
   a light emitting element for emitting light to a surface of a body, and
   a receptor element for detecting the light emitted from said light emitting element and reflected back from the body;

a light transmittance plate disposed on a first side of said receptor element and a first side of said light emitting element facing the body, wherein an outside surface of said light transmittance plate faces the body;

a main unit comprising a data processor for obtaining pulse information in accordance with a pulse signal detection signal supplied from said sensor unit; and a sleeve-like sensor unit holding band, wherein said holding band is elastic in at least a circumferential direction, so as to secure said sensor unit against the surface of the body, wherein said light transmittance plate is arranged tightly against the surface of the body;

wherein said sensor unit holding band and said sensor unit are comprised to allow displacement between 2.0 mm and 3.0 mm from a position whereat said sensor unit is disposed to the surface of the body without applying any load thereto, to a position whereat said light transmittance plate is disposed tightly against the surface of the body by said sensor unit holding band.

* * * * *